(12) United States Patent
Danenberg

(10) Patent No.: US 11,773,447 B2
(45) Date of Patent: Oct. 3, 2023

(54) USE OF CIRCULATING CELL-FREE RNA FOR DIAGNOSIS AND/OR MONITORING CANCER

(71) Applicant: LIQUID GENOMICS, INC., Torrance, CA (US)

(72) Inventor: Kathleen Danenberg, Torrance, CA (US)

(73) Assignee: NANTHEALTH LABS, INC., Culver City, CA (US)

( * ) Notice: Subject to any disclaimer, the term of this patent is extended or adjusted under 35 U.S.C. 154(b) by 346 days.

(21) Appl. No.: 15/526,712

(22) PCT Filed: Nov. 13, 2015

(86) PCT No.: PCT/US2015/060602
§ 371 (c)(1),
(2) Date: May 12, 2017

(87) PCT Pub. No.: WO2016/077709
PCT Pub. Date: May 19, 2016

(65) Prior Publication Data
US 2018/0258489 A1    Sep. 13, 2018

Related U.S. Application Data

(60) Provisional application No. 62/080,022, filed on Nov. 14, 2014, provisional application No. 62/214,756, filed on Sep. 4, 2015, provisional application No. 62/233,935, filed on Sep. 28, 2015.

(51) Int. Cl.
| | | |
|---|---|---|
| *C12Q 1/6886* | (2018.01) | |
| *C12Q 1/6806* | (2018.01) | |
| *C12Q 1/686*  | (2018.01) | |

(52) U.S. Cl.
CPC ......... *C12Q 1/6886* (2013.01); *C12Q 1/6806* (2013.01); *C12Q 1/686* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 8,304,187 B2 | 11/2012 | Fernando | |
| 2008/0057502 A1 | 3/2008 | Kopreski | |
| 2008/0261292 A1 | 10/2008 | Kopreski | |
| 2012/0093730 A1* | 4/2012 | Malecki | A61K 49/048 424/9.2 |
| 2012/0149582 A1* | 6/2012 | Rava | C12Q 1/6806 506/2 |
| 2013/0029339 A1 | 1/2013 | Skog et al. | |
| 2013/0252835 A1 | 9/2013 | Koh et al. | |
| 2014/0242101 A1* | 8/2014 | Andersen | A61K 39/0005 424/185.1 |
| 2014/0302070 A1* | 10/2014 | Chen | A61K 39/12 424/185.1 |

FOREIGN PATENT DOCUMENTS

| | | |
|---|---|---|
| CA | 2 965 528 A1 | 5/2016 |
| CN | 104334742 | 2/2015 |
| CN | 107002132 A | 8/2017 |
| EP | 2316972 | 5/2011 |
| EP | 2 807 277 A2 | 12/2014 |
| EP | 3 218 523 B1 | 2/2020 |
| JP | 2013-538565 | 10/2013 |
| JP | 2017-538404 A | 12/2017 |
| KR | 10-2017-0083563 A | 7/2017 |
| WO | 2010/112316 A1 | 10/2010 |
| WO | 2010112316 | 10/2010 |
| WO | 2012/170715 A1 | 12/2012 |
| WO | 2013103889 | 7/2013 |
| WO | 2013113012 | 8/2013 |
| WO | 2014151006 | 9/2014 |
| WO | 2014/151006 A3 | 11/2014 |
| WO | 2015013244 | 1/2015 |
| WO | 2016/077709 A1 | 5/2016 |

OTHER PUBLICATIONS

Enard et al. (Science 2002 vol. 296 p. 340) (Year: 2002).*
Cobb et al (Crit Care Med 2002 vol. 30 p. 2711) (Year: 2002).*
Fernando et al. (Clinical Biochemistry vol. 45 2012 p. 1497) (Year: 2012).*
Streck, "Cell-Free RNA BCT".
Qin, "A novel blood collection device stabilizes cell-free RNA in blood during sample shipping and storage, BMC Research Notes", http://www.biomedcentral.com/1756-0500/6/380, 2013.
Qiagen, "The Rascreen® KRAS RGQ PCR Kit Instructions for Use (Handbook)" Jul. 2012.
Qiagen, "QIAamp® Circulating Nucleic Acid Handbook", Jan. 2011.
Qiagen, "miRNeasy Micro Handbook", Feb. 2012.
PCT/US2015/060602—International Search Report dated Feb. 12, 2016, 3 pages.
Qin et al., A Novel Blood Collection Device Stabilizes Cell-Free RNA in Blood During Sample Shipping and Storage, Sep. 26, 2013, BMC Res Notes, Author manuscript, pp. 1-8.
Qiagen, QIAamp Circulating Nucleic Acid Kit Handbook, Second Edition, Jan. 2011, Sample & Assay Technologies, p. 10, paragraph 2; Retrieved online on May 11, 2017 from <https://www.qiagen.com/us/shop/sample-technologies/combined-sample-technologies/preparation/qiaamp-circulating-nucleic-acid-kit/#resources>.

(Continued)

*Primary Examiner* — Katherine D Salmon
(74) *Attorney, Agent, or Firm* — Martin Fessenmaier; Umberg Zipser LLP

(57) ABSTRACT

The invention provides compositions, methods, and systems for using cell-free RNA for improved detection of rare cells and/or species that are useful for diagnosing and/or monitoring cancer. The invention also provides for compositions, methods, and systems for early detection of cells that are resistant and/or developing resistance to cancer therapies.

8 Claims, 20 Drawing Sheets

(56) References Cited

OTHER PUBLICATIONS

Qiagen, miRNeasy Micro Handbook, Feb. 2012, Sample & Assay Technologies, p. 7 para 2 para 5, p. 18 para 5; Retrieved online on May 11, 2017 from <http://qiagen.com/us/shop/sample-technologies/rna/rna-preparation/mirneasy micro-kit/#resources>.
Qiagen, therascreen KRAS RGQ PCR Kit Handbook, Version 1, Jul. 2012, p. 6 para 2, Sample & Assay Technologies, Retrieved online on May 11, 2017 from <https://www.qiagen.com/us/shop/detection-solutions/personalized-healthcare/therascreen-kras-rgq-pcr-kit-us/#resources>.
Streck, Cell-Free RNA BCT Instructions, Jun. 2015, p. 1 col. 1 par 5, Retrieved online on May 11, 2017 from <http://www.streck.com/resources/cell_stabilization/cell-free_RNA_BCT/01_Instructions_(IFU)/>.
First Office Action received for Korean Patent Application Serial No. 1020177014255 dated Mar. 11, 2019, 11 pages (Including English Translation).
Second Office Action received for Korean Patent Application Serial No. 1020177014255 dated Oct. 25, 2019, 12 pages (Including English Translation).
Diehl Frank et.al., "Circulating mutant DNA to assess tumor dynamics", Nature Medicine, 2008, vol. 14, No. 9, pp. 985-990 (Cited from Specification).
Kopreski Michael S. et al., "Detection of Tumor Messenger RNA in the Serum of Patients with Malignant Melanoma", Clinical Cancer Research, 1999, Vo. 5, No. 8, pp. 1961-1965 (Cited from Specification).
Baselga Jose et al., "Relationship between Tumor Biomarkers and Efficacy in EMILIA, a Phase III Study of Trastuzumab Emtansine in HER2-Positive Metastatic Breast Cancer Clinical Cancer Research" 2016, vol. 22, No. 15. pp. 3755-3763 (Cited from Specification).
International Preliminary Report on Patentability received for PCT Application Serial No. PCT/US2015/060602 dated May 26, 2017, 8 pages.
First Office Action received for Canadian Patent Application Serial No. 2965528 dated Jun. 5, 2018, 4 pages.
Second Office Action received for Canadian Patent Application Serial No. 2965528 dated Jul. 12, 2019, 4 pages.
First Office Action received for Chinese Patent Application Serial No. 201580061965.4 dated Apr. 2, 2020, 23 pages (Including English Translation).
First Office Action received for European Patent Application Serial No. 15859714.6 dated Oct. 30, 2018, 1 pages.
Extended European Search Report received for EP Patent Application Serial No. 15859714.6 dated Mar. 1, 2018, 8 pages.
First Office Action received for Auslialian Patent Application Serial No. 2015346185 dated Mar. 16, 2020, 5 pages.
Bettegowda et al., "Detection of Circulating Tumor DNA in Early- And Late-Stage Human Malignancies", Science Translational Medicine, Feb. 19, 2014, vol. 6, No. 224, pp. 1-13 (Cited from Specification).
Office Action received for Israeli Patent Application Serial No. 251875 dated Mar. 23, 2020, 6 pages (Including English Translation).
Extended European Search Report received for EP Patent Application Serial No. 19218066.9 dated Apr. 22, 2020, 9 pages.
Notice of Reasons for Rejection received for Japanese Patent Application Serial No. 2017526583 dated Dec. 4, 2018, 6 pages (Including English Translation).
Notice of Reasons for Rejection received for Japanese Patent Application Serial No. 2017526583 dated Aug. 20, 2019, 9 pages (Including English Translation).
Communication under Rule 71(3) EPC received for European Patent Application Serial No. 15859714.6 dated Aug. 20, 2019, 59 pages.
Notice of Final Rejection Korean Patent Application Serial No. 1020177014255 dated Jun. 29, 2020, 11 pages (Including English Translation).
Danenberg et al., "PD-L1 gene expression and total cell-free RNA measured in blood positively differentiate healthy individuals from metastatic NSCLC patients", 2015, 1 page.

\* cited by examiner

Figure 5 (con't)

| Assay | Sample | Target/Total | CI Target/Total | Copies/μL (VIC) | CI Copies/μL (VIC) | Precision (VIC) |
|---|---|---|---|---|---|---|
| G12D | S1053 | 63.93% | 60.46% – 67.39% | 1056.5 | 1035.8 – 1077.6 | 2.00% |

| Copies/μL (FAM) | CI Copies/μL (FAM) | Precision (FAM) |
|---|---|---|
| 1872.5 | 1838.4 – 1907.3 | 1.85% |

Figure 13
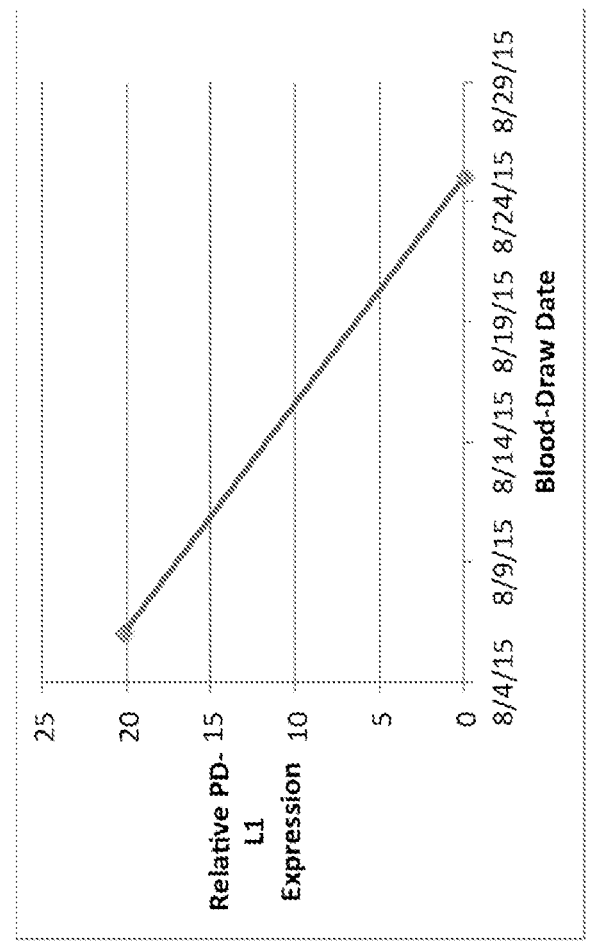
Fig. 13B
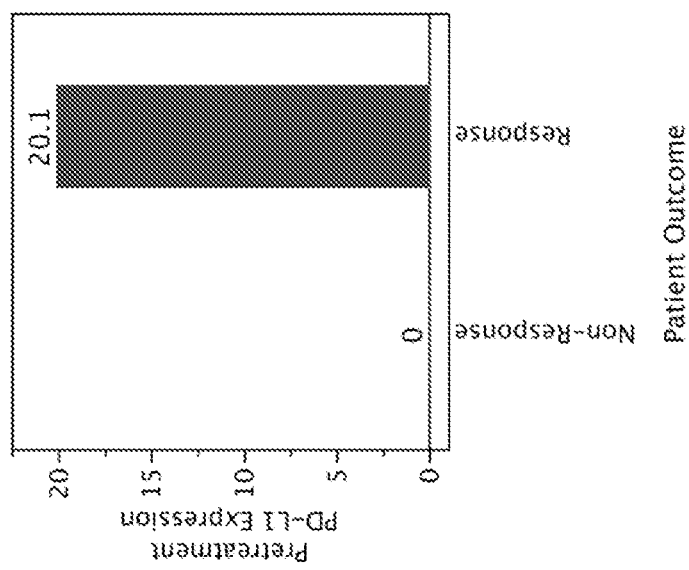
Fig. 13A

Figure 14
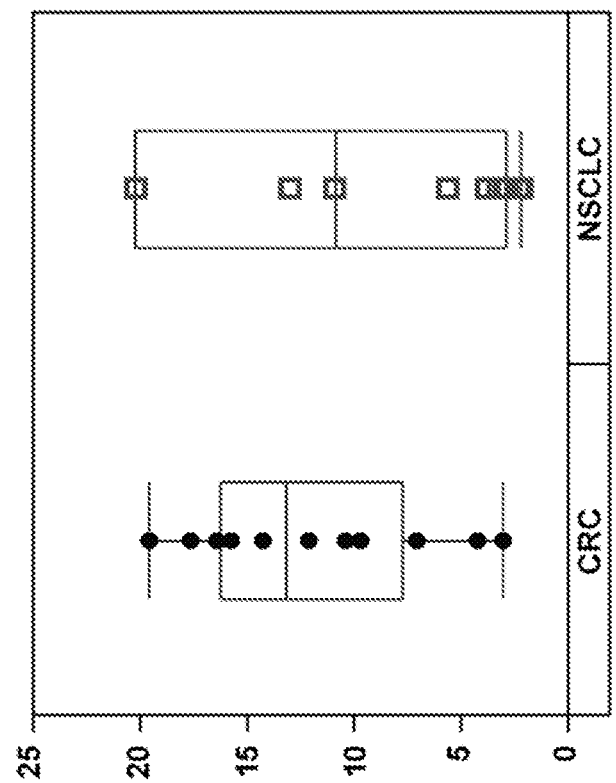
Fig. 14B
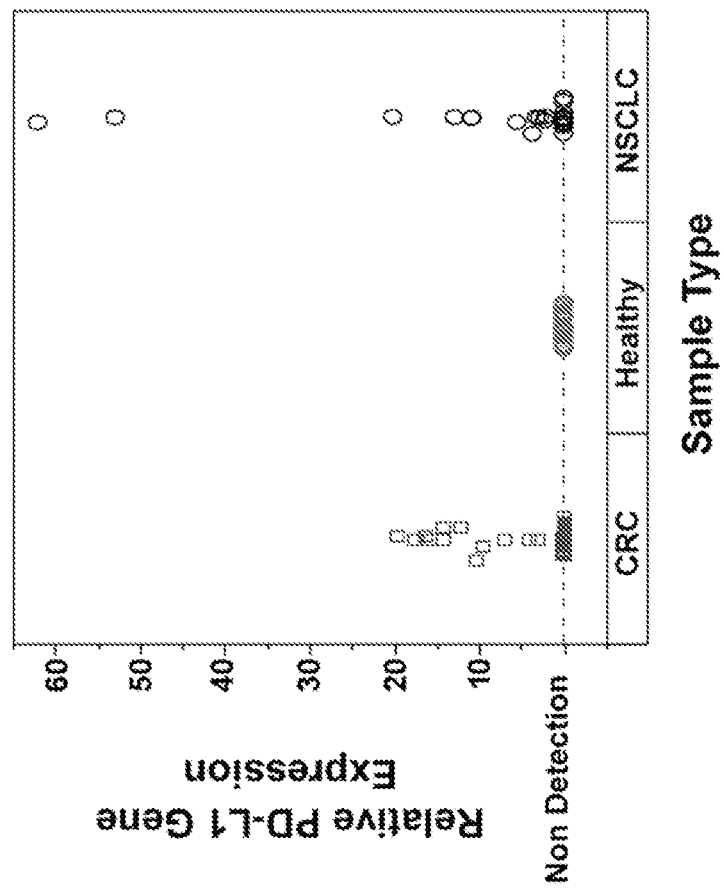
Fig. 14A

USE OF CIRCULATING CELL-FREE RNA FOR DIAGNOSIS AND/OR MONITORING CANCER

CROSS-REFERENCE TO RELATED APPLICATIONS

This application claims the benefit of U.S. Provisional patent applications 62/080,022, filed on Nov. 14, 2014, 62/214,756, filed on Sep. 4, 2015, and 62/233,935, filed Sep. 28, 2015, the contents of which are hereby incorporated by reference in their entirety.

FIELD OF THE INVENTION

The invention relates to the use of cell-free nucleic acids, particularly, cell-free RNA, for diagnosing and/or monitoring various types of cancer.

BACKGROUND OF THE INVENTION

The existence of cell-free (cf) nucleic acids, both DNA and RNA, in human blood has been known and studied since the late 1940s. The mechanism by which these molecules are released into the bloodstream is not quite clear yet. It may be a result of apoptosis and necrosis of cells from different tissues, or in the case of RNA, the nucleic acid may be contained in and protected from RNases in vesicles that are secreted into the blood. The utility of cell-free DNA (cfDNA) has recently been powerfully demonstrated in the ability to both diagnose cancer and monitor the response of cancer treatment. Recent developments in PCR-based sequencing technology, such as next generation sequencing, have made it possible to detect mutations in cfDNA and thus identify cancer pre-disposition mutations as well as cancer driver mutations. Conventional tumor tissue biopsies often cannot be obtained for logistic or medical reasons. When tumor tissue specimens from metastatic cancer patients are unavailable, liquid biopsies (e.g., blood) offer an alternative that can be rapidly implemented without the pain, risk, and expense entailed by a biopsy of one of the metastatic lesions (Bettegowda C et al. Detection of Circulating Tumor DNA in Early- and Late-Stage Human Malignancies. *Sci Transl Med* 2014; 6, (224). The relative ease of obtaining blood samples compared to tumor tissue biopsies now makes it possible to easily perform serial analyses of tumor DNA and thus to follow the emergence of drug-resistant clones as the tumor adapts to the initial treatment and begins to recur. Re-analysis of the patient's cfDNA might then identify new cancer driver mutations that have emerged, allowing new directed therapies to be designed.

One challenge has been the sensitivity of cfDNA analysis—in many cases, the mutation present in tumor tissue cannot be found in the blood because the cfDNA cannot be detected. Thus, one problem to be solved is an improved detection method so that low levels of cell-free nucleic acids, e.g., cell-free RNA (cfRNA), can be detected, particularly for the rare population of cells that are a small part of the overall population of cells in the biological sample being tested. A solution that achieves increased sensitivity for rare types of cells is particularly useful for diagnosing and/or monitoring resistant cells, for example, those cells found in individuals with cancer who are developing resistance to one or more cancer drug(s).

Another challenge is the sensitive detection of rare species that can be accomplished with a standard amount of plasma is typically collected from patients. The fraction of patients with detectable cfDNA represents the maximum currently obtainable from the amount of plasma collected. In the case of low secretion, one could try to use more and more plasma to isolate detectable cfDNA, however, this approach is not practical. As such, improvements in the methodology used for mutation detection might allow a greater percentage of tumors to be analyzed.

Furthermore, currently, tumors are sampled with a tumor biopsy, which produces static information regarding one tumor site. One tumor site may not be indicative of an individual's state of resistance towards cancer therapies. Similarly, one static snapshot in time may not be indicative of the present state of resistance towards cancer therapies or its likelihood of developing into such resistance. What is needed is a non-invasive way of sampling tumors so that there is increased sensitivity for detection of rare species. Furthermore, this way should also be able to provide dynamic information about tumors as they evolve into potential resistant stages toward cancer therapies. The invention described in this specification provides all of the foregoing and provides additional benefits as well.

Throughout the specification, various publications, patents, patent applications and other references are cited. All of these publications, patents, patent applications and other references are incorporated by reference in their entirety for all purposes.

SUMMARY OF THE INVENTION

The invention provides, inter alia, compositions, methods, and systems for improved detection of cell-free nucleic acid, particularly cell-free RNA (cfRNA) for identifying rare species that can be useful for diagnosing and/or monitoring various types of cancer.

Accordingly, in one aspect, the invention provides for methods for identifying one or more biomarkers associated with cancer in a biological sample from an individual having or suspected of having cancer, said method comprising: (a) isolating RNA from the biological sample using solid support, wherein the biological sample has been interacted with RNA stabilizer; (b) digesting existing DNA from the biological sample while RNA is on the solid support; (c) eluting RNA at least once from the solid support; (d) reverse transcribing the RNA to cDNA; (e) reacting the cDNA with at least one primer that is specific for detecting one or more biomarkers associated with cancer; and (f) determining whether one or more biomarkers are present in the biological sample, wherein the presence of the biomarker identifies whether the individual has one or more biomarkers associated with cancer. In some embodiments, the eluate of step (c) is passed over the same column for a dual elution. In other embodiments, the biological sample is plasma from the individual having or suspected of having cancer. In other embodiments, the plasma is processed within 7 days of interacting with the RNA stabilizer. In other embodiments, random hexamers are used in step (d) to reverse transcribe the RNA to cDNA. In other embodiments, the biomarker is a mutation in a gene or fusion transcript or gene expression selected from the group consisting of PD-L1, ERCC1, EGFR, TS, AREG, EREG, VEGFR2, EML4ALK, ROS1, RET, c-Met, FGFR1, KRAS, BRAF, NRAS, Her-2, PIK3CA, KIT, GNAQ, and GNA11. In other embodiments, the cancer is selected from the group consisting of cancer, lung cancer, melanoma, gastric, esophageal, breast, ovarian, sarcoma, renal cell, prostate, gastrointestinal stromal tumor (GIST) and pancreatic cancer.

In other aspects, the invention provides methods of increasing sensitivity of detection of one or more somatic mutation(s) associated with resistance to chemotherapy in cell-free RNA (cfRNA) in a biological sample from an individual having or suspected of having cancer, said method comprising: (a) isolating RNA from the biological sample using solid support, wherein the biological sample has been interacted with RNA stabilizer; (b) digesting existing DNA from the biological sample while RNA is on the solid support; (c) eluting RNA at least once from the solid support; (d) reverse transcribing the RNA to cDNA; (e) reacting the cDNA with at least one primer that is specific for detecting one or more of somatic mutation(s) associated with resistance; and (f) determining whether one or more somatic mutation(s) are present in the biological sample, wherein the presence of the somatic mutation(s) identifies whether the individual has one or more somatic mutation(s) associated with resistance to chemotherapy.

In other aspects, the invention provides methods of determining the likelihood of an individual having cancer or suspected of having cancer, said method comprising: (a) isolating RNA from a biological sample from the individual, wherein the biological sample has been interacted with RNA stabilizer; (b) digesting existing DNA from the biological sample while RNA is on the solid support; (c) eluting RNA at least once from the solid support; (d) reverse transcribing the RNA to cDNA; (e) reacting the cDNA with at least one primer that is specific for detecting one or more biomarkers associated with cancer; and (f) detecting whether one or more biomarkers associated with cancer are present in the biological sample, wherein the presence of the biomarker determining the likelihood of the individual having cancer.

In other aspects, the invention provides methods of aiding in the diagnosis of the likelihood of an individual having cancer or suspected of having cancer, said method comprising: (a) isolating RNA from a biological sample from the individual, wherein the biological sample has been interacted with RNA stabilizer; (b) digesting existing DNA from the biological sample while RNA is on the solid support; (c) eluting RNA at least once from the solid support; (d) reverse transcribing the RNA to cDNA; (e) reacting the cDNA with at least one primer that is specific for detecting one or more biomarkers associated with cancer; and (f) detecting whether one or more biomarkers associated with cancer are present in the biological sample, wherein the presence of the biomarker aids in the diagnosis of the likelihood of the individual having cancer.

In any of the embodiments, the eluate of step (c) is passed over the same column for a dual elution. In any of the embodiments, the biological sample is plasma from the individual having or suspected of having cancer. In other embodiments, the plasma is processed within 7 days of interacting with the RNA stabilizer. In any of the embodiments, random hexamers are used in step (d) to reverse transcribe the RNA to cDNA. In any of the embodiments, the somatic mutation is a gene or fusion transcript or gene expression selected from the group consisting of PD-L1, ERCC1, EGFR, TS, AREG, EREG, VEGFR2, EML4ALK, ROS1, RET, Met, FGFR1, KRAS, BRAF, NRAS, Her-2, PIK3CA, KIT, GNAQ, and GNA11. In any of the embodiments, the biomarker is a mutation in a gene or fusion transcript or gene expression selected from the group consisting of PDLAR-V7, -1, PD-L1, ERCC1, EGFR, TS, AREG, EREG, VEGFR2, EML4ALK, ROS1, RET, c-Met, FGFR1, KRAS, BRAF, NRAS, Her-2, PIK3CA, KIT, GNAQ, and GNA11. In any of the embodiments, the cancer is selected from the group consisting of cancer, lung cancer, melanoma, gastric, esophageal, breast, ovarian, sarcoma, renal cell, prostate, gastrointestinal stromal tumor (GIST) and pancreatic cancer.

BRIEF DESCRIPTION OF THE DRAWINGS

FIG. 13A shows pre-treatment PD-L1 expression for cell-free RNA (cfRNA) in high and no response patients prior to treatment. FIG. 13B shows an expected decrease in PD-L1 expression in cfRNA over the course of treatment in a responding patient.

FIG. 14A shows the relative frequency of PD-L1 gene expression in colorectal cancer (CRC), non-small cell lung cancer patents (NSCLC) and healthy individuals, 17.4% of CRC patients, 50% of NSCLC patients, and 0% of healthy individuals have relative increases in PD-L1 expression. FIG. 14B shows that relative PD-L1 gene expression levels are similar between PD-L1 positive CRC and NSCLC patients.

FIG. 15A shows an increase in allele fraction monitoring cfDNA for KRAS G12V throughout treatment of colorectal cancer with Regorafenib/Cetuximab. FIG. 15B shows that over time in the course of treatment there is a decrease in relative expression of PD-L1 in cfRNA during treatment of colorectal cancer with Regorafenib/Cetuximab. FIG. 15C shows the relative expression of ERCC1 over time during treatment of colorectal cancer with Regorafenib/Cetuximab.

Figure 16:
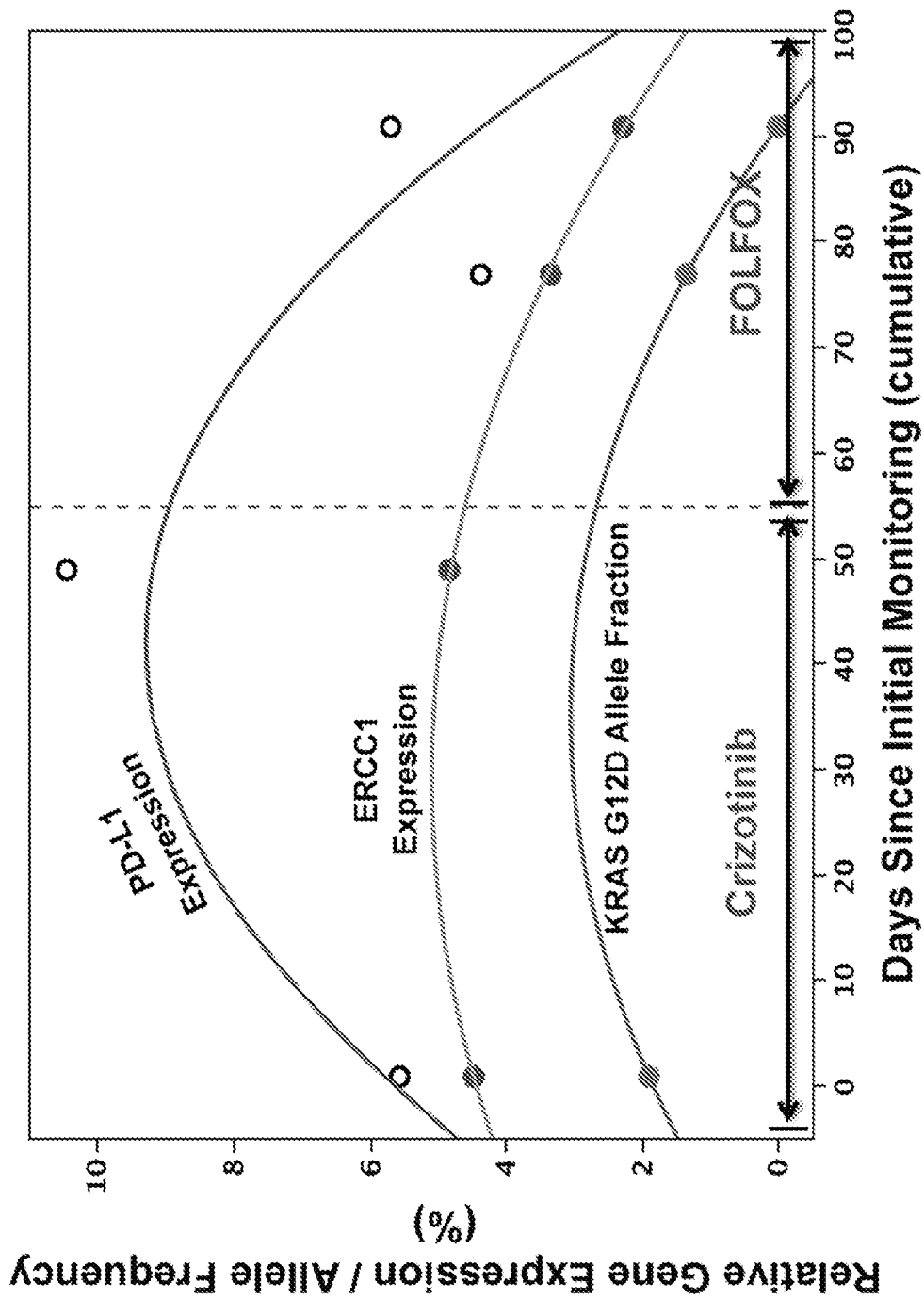

FIG. 16 shows relative gene expression from cfRNA in colorectal cancer patients during treatment with crizotinib and FOLFOX for PD-L1, ERCC1, and KRAS G12D.

Figure 17:
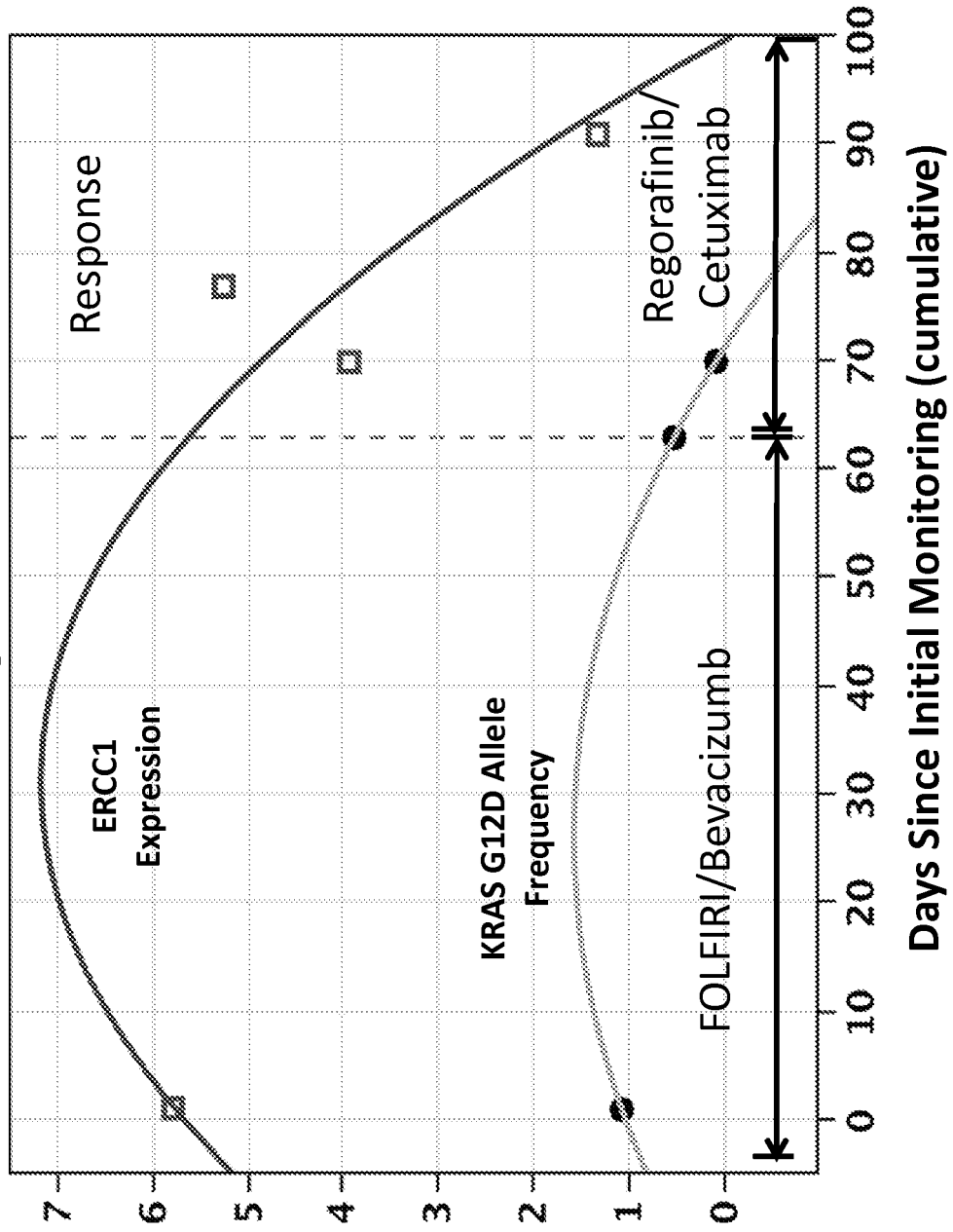

FIG. 17 shows relative gene expression from cfRNA in colorectal cancer patients during treatment with FOLFIRI/Bevacizumab and Regorafenib/Cetuximab for ERCC1, and KRAS G12D.

Figure 18:
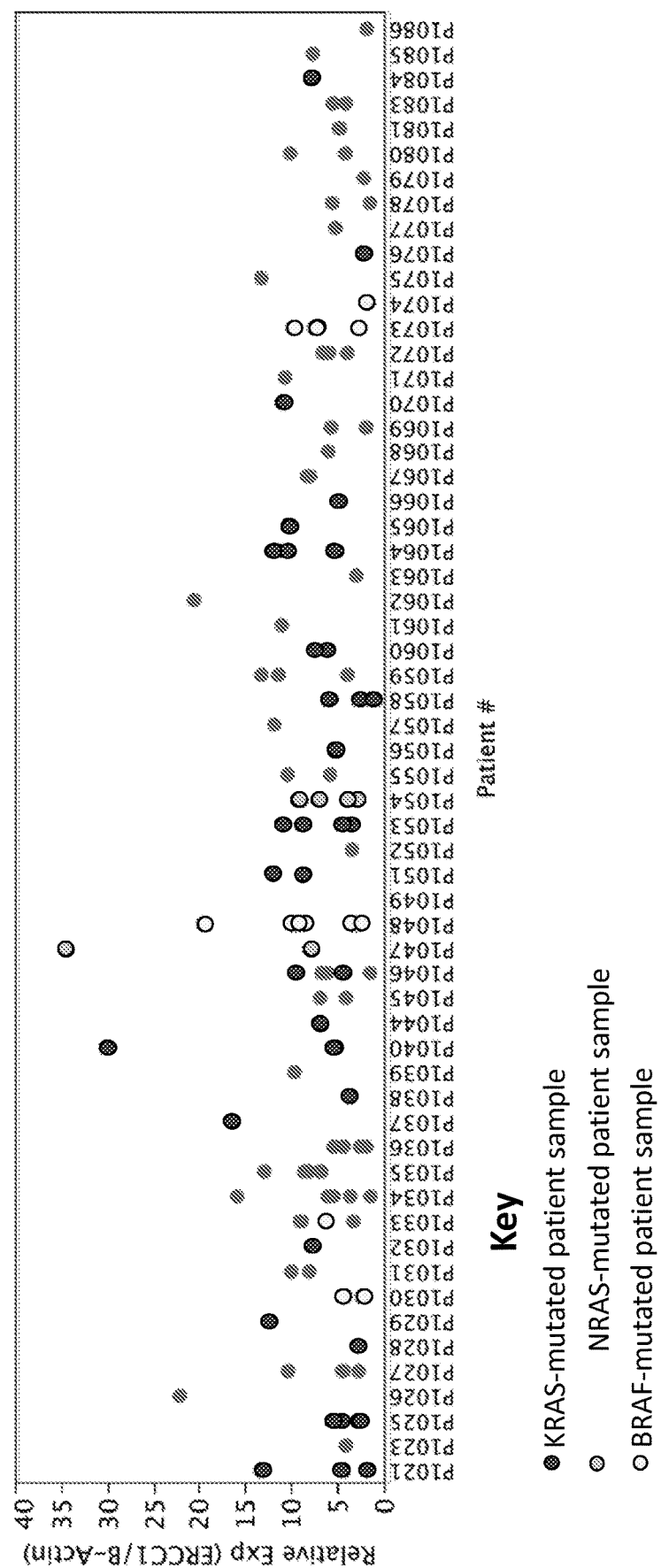

FIG. 18 shows relative expression of ERCC1 in patients with KRAS (red), NRAS (green), BRAF (yellow), or no (blue) mutations.

Figure 19:
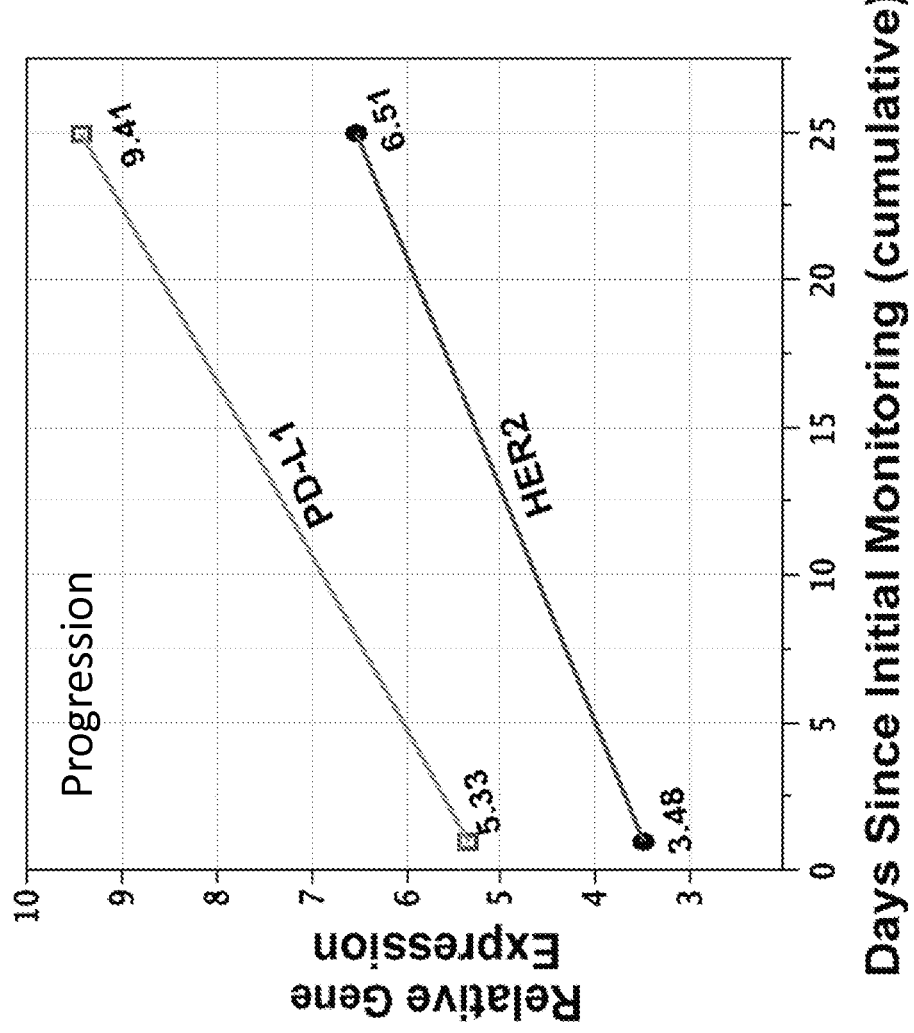

FIG. 19 shows relative expression monitored in cell-free RNA of PD-L1 and HER2 in a patient with gastric cancer.

DETAILED DESCRIPTION OF THE INVENTION

The invention provides, inter alia, compositions, methods, and systems for improved detection of cell-free nucleic acid, particularly cell-free RNA (cfRNA) for identifying rare species that can be useful for diagnosing and/or monitoring various types of cancer. For reasons further detailed herein, in various embodiments, the RNA species can be better to use than DNA species for diagnosis and/or monitoring various types of cancer. The ability to detect prominent species of RNA is generally well-known. However, the ability to detect the minor (or rare) species of RNA with increased sensitivity is a problem that has not been solved effectively to date.

Generally, it is accepted that RNA is difficult to work with in the clinical and laboratory setting. Numerous references document problems with RNA degradation and challenges dealing with processing the RNA. The invention disclosed here overcomes these existing challenges and provides ways to detect rare RNA species in a manner that is sensitive, rapid, accurate and provides useful information for dynamic diagnostic and/or monitoring (instead of static diagnostic and/or monitoring).

General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); *Antibodies: A Laboratory Manual*, Second edition, Cold Spring Harbor Laboratory Press, Cold Spring Harbor, N.Y. (Greenfield, ed., 2014), Beaucage et al. eds., *Current Protocols in Nucleic Acid Chemistry*, John Wiley & Sons, Inc., New York, 2000, (including supplements through 2014) and *Gene Transfer and Expression in Mammalian Cells* (Makrides, ed., Elsevier Sciences B.V., Amsterdam, 2003).

Definitions

Unless defined otherwise herein, all technical and scientific terms used herein have the same meaning as commonly understood by one of ordinary skill in the art to which this invention pertains.

As used herein, the term "biological sample" encompasses any sample taken from the individual (e.g., patient). Examples of biological sample include, but are not limited to, blood, plasma, tissue samples, serum, and bodily fluid.

As used herein, the term "protein" includes polypeptides, peptides, fragments of polypeptides, and fusion polypeptides.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. It is also intended that when reciting a range of numbers, then the numbers that fall within the range are also be included as if each individual number were all expressly written herein.

Compositions and Methods for Increased Detection of RNA

RNA was originally thought to be highly labile, easily degradable, and therefore not likely to be stable or detectable outside of the protective cellular environment. While DNA contains one copy (or several in the event of amplification) copies of a gene, transcription of a gene is likely to yield many copies of that gene in the form of mRNA. The mRNA contains the same genetic information as in the transcribed region of the DNA, so the same mutation must be present in both molecules. Theoretically, then, if a gene is transcribed 100 times, the sensitivity of detection of that mutated gene should also increase 100 times. One determinant of the success of cfRNA analysis is whether sufficient tumor-originated cfRNA for diagnostic analysis exists in the blood and whether it can be readily and successfully isolated. Accordingly, following the methodology described herein, it is possible to obtain results where as much as 30-60 fold more RNA is detected than DNA from the circulating nucleic acids. This is useful for many utilities, one of which is that tumor-specific mutations can be detected in the resulting cDNA.

As exemplified in Example 1, one of skill in the art can detect cell-free RNA, particularly of minor or rare RNA species according to the following methodology. One of skill in the art should be able to understand that various substitutions and minor deviations can be used that would still be within the scope of the invention. From individuals that have cancer or are suspect of having cancer, a biological sample (e.g., blood) is obtained. In some embodiments, the individual that has cancer or is suspected of having cancer is a patient that is under the care of one or more physicians. The biological sample is mixed, contacted, interacted, and/or processed with an RNA stabilizer. Various exemplary RNA stabilizers can be used. Various RNA stabilizers can be used in the compositions and methods of the invention. One exemplary standardized method for sample collection, stabilization, and transport of cell-free plasma RNA that can be used is the Cell-Free RNA BCT® from Streck. Other RNA stabilizers that can be used include, but are not limited to, Biomatrica RNA Guard (Biomatrica) <http://www.biomatrica.com/rnagardblood_tube.php>, Paxgene blood RNA tube (Becton Dickinson) <http://www.preanalytix.com/products/blood/RNA/paxgene-blood-ma-tube>, Tempus Blood RNA Tube (Life Tech) <http://www.lifetechnologies.com/order/catalog/product/4342792>, and RNA/DNA Stabilization Reagent for Blood/Bone/Marrow (Roche) <http://lifescience.roche.com/shop/products/ma-dna-stabilization-reagent-for-blood-bone-marrow>.

The plasma can be separated from other blood layers by various methods known to one of skill in the art (e.g., centrifuge, spinning, etc.). In one embodiment, the plasma layer is removed from the buffy coat. The timing of the separation can be within a short period of time from the drawing blood from the individual. In some embodiments, the period of time is within about 1 minute, 2 minutes, 3, 4, 5, 6, 7, 8, 9, or 10 minutes. In other embodiments, the period of time is within about 10-15 minutes, 15-30 minutes, 30-45 minutes, 45 minutes-1 hour, 1-24 hours, 1 day, 2 days, 3 days, 4 days, 5 days, 6 days and 7 days. Additional plasma can be frozen and used at a different time as needed.

In some embodiments, the plasma is processed within about 1 minute, 2 minutes, 3, 4, 5, 6, 7, 8, 9, or 10 minutes of interacting with an RNA stabilizer. In other embodiments, the period of time is within about 10-15 minutes, 15-30 minutes, 30-45 minutes, 45 minutes-1 hour, 1-24 hours, 1 day, 2 days, 3 days, 4 days, 5 days, 6 days and 7 days.

The nucleic acid (e.g., RNA) then is extracted from the biological sample, e.g., plasma. Various methods can be used to extract the RNA. Exemplary protocol in Example 1 can be used. Other commercially available kits may be used to extract the RNA. In one embodiment, the extraction uses solid support, such as a column. In one embodiment, the DNA can be digested on the column by using DNAse digestion. Elution can be achieved by standard techniques known to one of skill in the art. An exemplary protocol can be found in Example 1. In one embodiment, the same eluate from the column is passed over the same column again for a dual elution step. In another embodiment, the methodology has the combination of contacting the blood with RNA stabilizers, processing the plasma within 3 days of separating from blood, using on-column DNAse digestion, and eluting the RNA from the column twice (or more).

The resultant RNA can be reverse transcribed to cDNA by standard methods known to one of skill in the art. An exemplary protocol can be found in Example 1. Random hexamers can be used. Further amplification of the RNA can occur when it is converted to cDNA, especially with the optional use of clamping sequences such as ZIP nucleic acids, which may be added to the reverse transcriptase primer to further increase the affinity of oligonucleotides for their target by decreasing the electrostatic repulsions due to the polyanionic nature of nucleic acids.

The resulting cDNA can be cleaned up and used for analysis. PCR and other amplification technique can be used to detect biomarkers specific for tumors and cancers, genes associated with tumors and cancers, and/or fusion transcripts seen in cancers and tumors. Gene expression of certain genes that are associated with cancer can be detected and quantitated as well and used to predict, determine, diagnose or aid in the diagnosis of cancers and tumors.

There are a number of important fusion transcripts that are targeted by specific chemotherapeutic agents. These include fusion partners of EML4-ALK, RET and ROS1. Blood-based assays measure DNA by PCR cannot detect the transcript fusions. The detection of mRNA in the blood will enhance the ability to monitor patients for fusion detection as it corresponds to drug sensitivity and the emergence of specific mutations in these fusions that can create resistance to the original chemotherapy regimen and sensitivity to another regiment.

Various algorithms can be used to quantitate yield of RNA by comparison with internal controls (e.g., beta actin, housekeeping genes). In one embodiment, relative expression of genes of interest can be determined through the difference of PCR cycle thresholds (Cts) of the gene of interest (using specific primers for that gene) minus the PCR cycle threshold of a stably expressed housekeeping gene such as beta actin. This method of quantitation is referred to as the delta delta Ct method of relative quantitation. The amount of target normalized to an endogenous reference and relative to a calibrator is given by $2^{-delta, deltaCt}$. ABI User Bulletin #2:ABI 7700 Sequence Detection System Dec. 11, 1997 (updated October 2001) <http://www3.appliedbiosystems.com/cms/groups/mcb_support/documents/generaldocuments/cms_040980.pdf.> For example, the relative expression of an EML4-ALK fusion mRNA can be expressed as a constant $(K) \times 2^{-(Ct(EML4ALK)-Ct(Beta\ Actin))}$ A multiplier constant K is set that generates a whole number for the median of each EML4-ALK fusion relative expression level $(2^{-(Ct(EML4ALK)-Ct(Beta\ Actin))})$ across multiple lung cancer samples. The relative expression of EML4-ALK fusion in unknown samples can be determined by comparing the results of the unknown sample with a known control sample with a set value for expression. If the known sample value is set at 10 and K is arbitrarily set at 100, the relative expression of the unknown sample, X, is calculated according to the following formula:

$$10 = K \times 2^{-(Ct(EML4ALK)-Ct(Beta\ Actin))(Delta\ Ct\ Known)}$$

$$X = K \times 2^{-(Ct(EML4ALK)-Ct(Beta\ Actin))(Delta\ Ct\ Unknown)}$$

Relative Expression of Unknown=$X$=10× $2^{-deltaCt\ Unknown}/2^{-deltaCt\ Known}$ For each PCR plate run, the value of the multiplier K can be adjusted to correct for PCR plate to plate variations in the relative expression of a known sample so that the value for the known sample remains exactly at the set point, 10.

In another embodiment, a standard curve of PCR products employing known amounts of EML4-ALK fusion DNA fragments spiked into a constant amount of DNA without fusions can be employed to act as a control for comparing relative expressions of unknown samples to controls with known expressions of EML4-ALK. A plot of Cts of known samples on the Y axis vs log 10 relative expression of known EML4-ALK controls on the X axis will generate a linear curve described by the following equation:

$Ct_{EML4-ALK}$=Slope×$X_{(relative\ expression\ EmI4-ALK)}$+$Y$ intercept

Solving for $X$ (the relative expression of an unknown sample)

$X$=Relative expression$_{unknown\ sample}$= ($Ct_{unknown\ sample}$−$Y$ intercept of std curve)/Slope of std curve Quantitation of Minor or Rare Species In some aspects of the invention, the composition and methodology described herein can be used to quantitate cell-free nucleic acid, particularly cell-free RNA. Quantitation can be achieved for major as well as minor species of RNA. The challenge facing accurate diagnosis is the detection of minor (or rare) species of RNA that can be predictive, diagnose, and/or aid in the diagnosis for resistance to cancer therapy and/or indicate the emergence of a mutant or resistant cell(s). In some aspects of the invention, minor species of RNA that can be detected are present in about 0.01% to 60% of wild type RNA. In some embodiments, the minor species of RNA that can be detected are present in at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% of wild type RNA. In other embodiments, the minor species of RNA that can be detected are present in at least about 2%, 3%, 4%, 5%, 6%, 7%, 8%, 9%, 10%, 11%, 12%, 13%, 14%, 15%, 16%, 17%, 18%, 19%, or 20% of wild type RNA. In other embodiments, the minor species of RNA that can be detected are present in at least about 21%, 22%, 23%, 24%, 25%, 26%, 27%, 28%, 29%, or 30% of wild type RNA. In other embodiments, the minor species of RNA that can be detected are present in at least about 31%, 32%, 33%, 34%, 35%, 36%, 37%, 38%, 39% or 40% of wild type RNA. In other embodiments, the minor species of RNA that can be detected are present in at least about 41%, 42%, 43%, 44%, 45%, 46%, 47%, 48%, 49%, or 50% of wild type RNA. In other embodiments, the minor species of RNA that can be detected are present in at least about 51%, 52% 53%, 54%, 55%, 56%, 57%, 58%, 59% or 60% of wild type RNA. In any of the embodiments above, the minor species of RNA that can be detected are present in at most about any of the percentages indicated above and also in ranges that include combination of lower limit and upper limit from any of the percentages indicated above.

Using Cell-Free RNA for Diagnostic and/or Monitoring for Oncology

Described herein are compositions, systems and methods for diagnosing and/or monitoring various types of cancer using cell-free nucleic acids, particularly cell-free RNA. cfRNA can be useful for diagnosing an individual (e.g., a patient under a physician's care) having cancer or suspected of having cancer to determine what type of cancer they have and/or to determine if they have any mutations associated with cancer (i.e. cancer biomarker) and/or to determine if they have (or are developing) a resistant phenotype or resistant genotype to cancer therapeutics. In addition, the compositions, systems and methods disclosed herein can be used to monitor individuals over time (e.g., longitudinal course) to quickly detect when a resistant phenotype or resistant genotype is emerging. The accuracy and specificity of the diagnosis and/or monitoring is achievable by using cfRNA that is not readily achievable using cfDNA. As further described herein, the statistically significant difference in seen in cfRNA measurement between an individual with cancer and a healthy individual without overlap in the ranges of expression provides advantages for the detection (including early detection) of cancer and for monitoring for recurrence of cancer. As needed, the physician can take steps appropriate for addressing the emerging resistance to the cancer therapeutic drug or compound(s).

The specificity of mutation detection in blood DNA can be close to 100%, that is, the mutations found in blood DNA almost always reflect those in the DNA obtained from the actual tumor tissue. However, one problem is that the sensitivity of current cfDNA analysis is generally less than 100%; that is, in many cases, the mutation present in the tumor tissue cannot be found in the blood because the cfDNA is not detected. For example, in one study, cfDNA was detectable in >75% of patients with advanced pancreatic, ovarian, colorectal, bladder, gastroesophageal, breast, melanoma, hepatocellular, and head and neck cancers, but in less than 50% of primary brain, renal, prostate, or thyroid cancers, while in patients with localized tumors, cfDNA was detected in 73%, 57%, 48%, and 50% of patients with colorectal cancer, gastroesophageal cancer, pancreatic cancer, and breast adenocarcinoma, respectively (Bettagowda, 2012).

Without being bound by theory, the lack of cfDNA detection could be due to the following non-limiting reasons: 1) some cancers do not secrete any DNA into the bloodstream, or 2) all tumors secrete some cfDNA but the amount of DNA emanating from some tumors is too small to be detected by current technology. Without being bound by theory, the latter possibility can be because a characteristic of tumors is that cells turn over rapidly, dying as rapidly as they are formed, thus accounting for the generally higher levels of nucleic acids found in the blood of cancer patients. Furthermore, cfDNA secretion by tumors is known to vary over a very wide range. One study using a specially designed sensitive detection method found cfDNA in all of 18 colorectal cancer patients ranging from 1.3 to 23,000 mutant templates per sample (median 99 mutant templates per sample; range between 10th and 90th percentiles, 3-2,837). This study concluded that "most previous studies have not used techniques sufficiently sensitive to detect the low levels of cfDNA found in many of the subjects evaluated in the current study" (Diehl F et al. Circulating mutant DNA to assess tumor dynamics. *Nat Med.* 2008; 14:985-990).

As described herein, the use of cfRNA presents opportunities to access potentially valuable and useful information that cannot be obtained from DNA analysis. Whereas mRNA expression is highly regulated in normal cells, it becomes increasingly dysregulated in the progression toward cancer. Thus, without being bound by theory, there should be many genes that are highly expressed in tumors that are not highly expressed in normal tissue. An earlier study showed that tyrosinase mRNA could be detected at high levels in the serum of cancer patients but not in non-cancerous individuals (Kopreski M S et al. Detection of tumor messenger RNA in the serum of patients with malignant melanoma. *Clin Cancer Res.* 1999; 8:1961-5). Similar to tyrosinase mRNA, other tumor mRNA should be demonstrable in serum and plasma in other malignancies. In another study, thymidylate synthase (TS) expression was measured in plasma from 88 patients and 26 controls by quantitative PCR. TS mRNA was detected in plasma in 47% of patients, showing significant differences from healthy controls. Notably, patients with TS mRNA in plasma had higher levels of TS in tumor tissue than patients without.

Accordingly, in one aspect, mRNA (gene expression) measurements using cfRNA can be useful to detect an abnormal expression of one or more cancer-associated gene (s) and/or alleles and/or mutations. Such detection can be used to diagnose the presence (or absence) of disease, or to assess the status of the cancer. In one embodiment, cell free mRNA levels are higher compared to DNA.

A "Liquid Biopsy"—using peripheral blood to obtain timely information on genetic information in solid malignancies, contains dynamic DNA and RNA information from all tumor sites and is not limited to the area of biopsy.

In another embodiment, gene expression could also be useful for monitoring the course of chemotherapy. While DNA is largely a static molecule in terms of alterations (that is, new mutations in DNA can take a long time to appear), changes in gene expression can occur rapidly, in a matter of days or even hours, and thus may provide a rapid and sensitive means of assessing changes in the tumor, such as those brought about by the effects of drugs. A continuum of values for relative expression (increasing, decreasing or static levels) of the fraction of rare or aberrant transcripts with respect to normal or wild type transcripts can be measured over time in plasma from the individual (e.g., patient). Upward or downward trends of expression can be linked to patient outcome to specific chemotherapy regimens.

Chemotherapy regimens can differ by cancer type, stage, and patient genetics. Chemotherapy can be tailored to specific tumor phenotype. Methods of the present invention can be used to monitor response to a specific chemotherapy regimen prior to, throughout, and following treatment. Example chemotherapy regimens included, but are not limited to treatment of PD-L1 positive cancer with nivolumab; treatment of CRC with Regorafenib/Cetuximab; crizotinib; FOLFOX; FOLFORI/Bevacizumab; and Regorafinib/Cetuximab.

In yet another embodiment, the invention provides for quantitatively determining expressions of drug response determinant genes can predict the effectiveness of drugs and thus could be used for making treatment decisions. For example, a recent study showed that advanced HER2-positive breast tumors expressed variable amounts of HER-2 and patients with the highest level of expression derived a dramatically better survival benefit from a Herceptin® than those with lower expressions (Baselga J, et al. Relationship between tumor biomarkers and efficacy in EMILIA, a phase III study of trastuzumab emtansine (T-DM1) in HER2-positive metastatic breast cancer. *AACR* 2013; Abstract LB-63). Moreover, activating mutations in PIK3CA, which blunt the effects of anti-HER-2 drugs such as lapatanib, had no effect on therapy with Herceptin®. If tissue expression levels of HER-2 of these breast cancer patients are reflected in their cfRNA, a blood draw rather than a tissue biopsy can be used to get information on expression of HER-2 as well as mutational status of PIK3; (4) for some cancer-associated biomarkers and/or genes (e.g., Her-2), the copy number may vary. This variation can be detected only with RNA; and (5) An additional problem with DNA analysis is that some chemotherapeutic agents are targeting cases of gene fusions which are only analyzable from RNA and cannot be measured in DNA. Non-limiting examples of these targets are gene fusions (e.g., EML4-ALK, ROS1, RET). By way of another example, for those patients with secondary changes like the T790M-mediated resistance to EGFR inhibitors irreversible tyrosine kinase inhibitors (TKI) seem to be a promising alternative.

Measurement of expressions of each variant or emerging resistance mutations in these genes from the plasma of patients undergoing therapy can be critical for optimal patient care. Specific drugs that are active in only certain fusions or mutations in these genes can be deployed to help the patient if rapid and accurate diagnosis of these gene fusions occur. Re-biopsy of patients undergoing therapy is not practical for these patients. This can be achieved using the cfRNA methodology as described herein.

Accordingly, non-limiting example of genes associated with response to chemotherapy that can be measured according to the methodology described herein include: EGFR, KRAS, BRAF, NRAS, JAK2, ALK, PDGFRA, IDH1, IDH2, and KIT. In some aspects of the invention, the biomarker is a mutation in a gene or fusion transcript selected from the group consisting of PD-L1, ERCC1, EGFR, TS, AREG, EREG, VEGFR2, EML4ALK, ROS1, RET, c-Met, FGFR1, KRAS, BRAF, NRAS, Her-2, PIK3CA, KIT, GNAQ, and GNA11.

In some embodiments of the invention, the individual has or is suspected of having colorectal cancer, lung cancer (e.g., non-small cell lung cancer), melanoma, gastric, esophageal, breast, ovarian, sarcoma, renal cell, prostate, gastrointestinal stromal tumor (GIST) and pancreatic cancers. In other embodiments, the gene that is detected and/or quantitated is listed below in Table 1.

TABLE 1

| RNA | Colon | Lung | Melanoma |
|---|---|---|---|
| PD-L1 | PD-L1 | PD-L1 | PD-L1 |
| ERCC1 | ERCC1 | ERCC1 | |
| EGFR | EGFR | EGFR | |
| TS | TS | TS | |
| AREG | AREG | | |
| EREG | EREG | | |
| VEGFR2 | VEGFR2 | | |
| EML4ALK | | EML4ALK | |
| ROS1 | | ROS1 | |
| RET | | RET | |
| ROS1 | | | |
| RET | | | |
| c-Met | | c-Met | |
| FGFR1 | | FGFR1 | FGFR1 |

In other embodiments, the gene and/or mutation that is detected and/or quantitated is listed below in Table 2.

TABLE 2

| RNA or DNA | Colon | Lung | Melanoma |
|---|---|---|---|
| KRAS | G12C | G12C | |
| KRAS | G12V | G12V | |
| KRAS | G12D | G12D | |
| KRAS | G12A | G12A | |
| KRAS | G12S | G12S | |
| KRAS | G13D | G13D | |
| KRAS | Q61H | | |
| EGFR | | L858R | |
| EGFR | | (Exon 19 Deletions) ΔE746-A750 | |
| EGFR | | L861Q | |
| EGFR | | T790M | |
| EGFR | | G719S | |
| BRAF | V600E | V600E | V600E |
| BRAF | | | V600K |
| NRAS | Q61K | | |
| NRAS | Q61L | | |
| NRAS | Q61R | | |
| HER2ins | | HER2 ins | |
| PIK3CA | H1047R | H1047R | |
| PIK3CA | H1047L | H1047L | |
| PIK3CA | E542K | E542K | |
| PIK3CA | E545K | E545K | |
| KIT | | | WQ577R |
| KIT | | | WQ577R |
| KIT | | | L576P |
| KIT | | | V559A |
| KIT | | | K642E |
| GNAQ | | | Q209L |
| GNA11 | | | Q209L |

Cell-free DNA (cfDNA) released into the bloodstream by tumors allows non-invasive identification of initial tumor-specific mutations. However, not all molecular changes in tumors involve DNA mutations; in many cases it is also the quantity of a particular gene (e.g., gene expression) that is important. In an embodiment, the use of cell-free RNA (cfRNA) released into the blood in order to monitor gene expression in cancer patients. In a particular embodiment, the PD-1/PD-L1 pathway is a promising therapeutic target and anti-PD-L1 agents have shown encouraging activity in a variety of tumor types.

To assess cell RNA quantity for a particular gene (e.g. PD-L1), plasma may be fractionated from patient collected blood. Methods of fractionating blood are known in the art and include as non-limiting examples fractionation by the Cohn method (e.g. cold ethanol fractionation), chromatography, or combinations thereof. Quantitative RT-PCR can be used with gene specific primers to quantitate a specific gene. Gene quantity for a gene of interest can be compared to health volunteers. Housekeeping genes such as, for example, β-actin as describe hereinabove, can be used as denominator genes that represent total RNA.

One of skill in the art can use the disclosure described herein to measure the expression of certain genes that for detection and/or diagnosis of cancer. As further detailed herein, some cancer biomarkers show a statistically significant difference for cfRNA measurement between individuals with cancer and healthy individuals. The lack of overlap in the ranges of expression between individuals with cancer and a healthy individuals allows for multiple uses, for example, for the detection (including early detection) of cancer and for monitoring for recurrence of cancer.

Composition, Kits and Systems

The invention also provides compositions for achieving highly sensitive detection so that emerging resistance mutations can be detected. In one aspect, a system is provided that includes not only the reagents for isolating biological samples (such as plasma), RNA stabilizer(s), extraction column(s), elution solution(s) but also the reagents needed for reverse transcription and primers/probes specific for tumor/cancer biomarkers. In some embodiments, the system is a kit that includes instructions for the methodology. Optionally, the system includes instructions for calculating the RNA yield of mutant, fusion transcripts and other rare transcripts with respect to normal or wild type transcripts.

The following examples are provided for illustrative purposes only and are not intended to limit the scope of the invention in any manner.

EXAMPLES

Example 1

The following describes exemplary protocols for cell-free RNA extraction, reverse transcription and PCR amplification procedure that were utilized in some embodiments. The protocols described below include modifications made by the inventors that were not described in manufacturer's instructions that came with the commercially available kits and/or reagents.

1) Draw blood from patient in Streck® RNA BCT tubes (with RNA stabilizer)
2) Centrifuge and separate cell-free RNA plasma from other blood layers within 7 days of drawing blood from the patient.
3) Remove plasma layer from buffy coat by carefully pipetting off top layer
4) Extract about 1-3 ml of plasma upon spin-down of plasma.
   Maximum amounts of RNA are recovered by extraction immediately after separating plasma from whole RNA stabilized blood.
5) Freeze excess plasma in 1 ml aliquots at −80 deg C.
6) Extraction of nucleic acid was done as follows:
   a. Using QIAamp® Circulating Nucleic Acid Kit
      i. Prepare buffers contained in kit: ACB, ACW1 and Buffer ACW2 with volumes required for number of samples to be isolated
      ii. Add carrier RNA (1 ug) to buffer ACL at volumes per reaction described in kit
      iii. Incubate Proteinase K and plasma at 60 degrees C. for 1 hour
      iv. Add buffer ACB to lysate
      v. Incubate on ice for 5 minutes
      vi. Apply mixture to QIAamp mini column and draw liquid through with vacuum
      vii. Apply 600 ul Buffer ACW1 to QIAamp Mini Column. Draw liquid through column with vacuum pump
      viii. Apply 750 ul of Buffer ACW2 to the QiaAmp Mini column. Draw liquid through using vacuum
      ix. Perform On column DNAse digestion of DNA by adding 60 ul RNAse Free DNAse directly to center of column and incubating on column for 15 minutes at room temperature.
   b. Prepare RNAse Free DNAse (Qiagen Cat. No. 79254) using 2.5 ul DNase stock, 10 ul RDD buffer, 87.7 ul Water (Rnase free).
      i. Repeat steps vii and vii above (6)(a)
         a. Apply 600 ul Buffer ACW1 to QIAamp Mini Column. Draw liquid through column with vacuum pump
         b. Apply 750 ul of Buffer ACW2 to the QiaAmp Mini column. Draw liquid through using vacuum
      ii. Additional steps:
         1. Apply 750 ul ethanol (96-100%) to the QIAamp mini column. Draw ethanol through with vacuum.
         2. Centrifuge mini column in a clean 2 ml tube to dry by centrifugation
         3. Further dry by heating column at 56 degrees C. for 10 minutes
      iii. Elution step
         1. Manufacturer suggested that elution be performed by placing 30 to 150 ul of buffer AVE to the center of QIAamp Mini membrane, incubating at room temperature for 3 min and centrifuging at 2,000×g for 1 min to elute nucleic acid.
         2. Manufacturer also suggested that DNA be digested in the eluate solution using DNAse free RNAse with a further cleanup using RNeasy Clean up columns. Results: This procedure was found to be unsuccessful and yielded very little to no RNA or resulting cDNA.
         3. Manufacturer strongly suggested that on-column DNAse treatment would not work. The inventors tried following manufacturer's suggestion for another commercially available product: Quantitect Reverse Transcription kit, which reverse transcribes as well as digests DNA in solution. Results: This Quantitect Reverse Transcription kit produced very little to no resulting cDNA signal when PCR amplified with beta actin primer/probes.
         4. The inventors eluted twice with same buffer and then
            a. Place 60 ul buffer AVE to the center of QIAamp Mini membrane, incubate at room temp for 3 min, centrifuge at 20,000×g for 1 min, remove eluate from collection tube, place it back on the QIAmp Mini membrane again, incubate for an additional 3 min and centrifuge to elute.

b. Since DNA was digested on the column, no cleanup was required.
5. Next, the RNA was reverse-transcribed to cDNA using the VILO reverse transcriptase kit (Life Technologies) and random hexamer primers, followed by bBinding of random hexamers at room temperature for 10 minutes, extension at 42 degrees C. for 60 minutes, heat killing of enzyme at 85 degrees C. for 15 minutes.
   a. Resulting cDNA iwas purified using ZYMO ssDNA and RNA cleanup columns per manufacturer's instructions. This can be done in some embodiments.
   b. PCR of cDNA using beta-actin primer/probes iwas used to determine relative amount of RNA. QUBIT reading of RNA concentrations gave the appearance of no RNA.
6. Resulting cDNA was PCR amplified with primer/probes developed to amplify RNA sequences rather than DNA by spanning introns when possible.
7. No RT controls (non-reverse transcribed RNAs) were run to rule out the presence of amplifiable DNA in the sample.
8. In another embodiment, robotic extraction techniques were used to isolate RNA from patient plasma.

Contrary to what was taught by manufacturer and the current state of the art with respect to the stability of RNA and how to treat RNA, the RNA extraction procedure utilizes a combination of RNA stabilized blood draw tubes, an on-column DNAse digestion, the dual elution of RNA (passing the first eluate back through the column to increase the yield) and the immediate processing of plasma separated from BCT stabilized blood. RNA is unstable in plasma even under frozen conditions. The BCT RNA stabilized tubes from Streck do not appear to protect the RNA from degradation after freezing.

Algorithms were developed to determine yields of RNA (reverse transcribed cDNA) by comparing CTs resulting from PCR of cDNA from plasma using beta-actin primer/probes and random hexamers with cDNA from known concentrations of controls such as Universal Human Reference (UHR) RNA from Agilent. Generally, a value is set for a known control cDNA to be included in each PCR run of unknown samples to determine the relative expression of the unknown samples. The delta-delta Ct method described in section 00033 is used for calculation of relative expressions. The controls can be purchased cell line RNA (such as UHR) or synthetic fragments of cDNA can be spiked into wild type or normal control cDNA for each gene of interest.

Primers and probes were employed to amplify the cDNA strand resulting from reverse transcription using random hexamers.

Example 2

Figure 1:
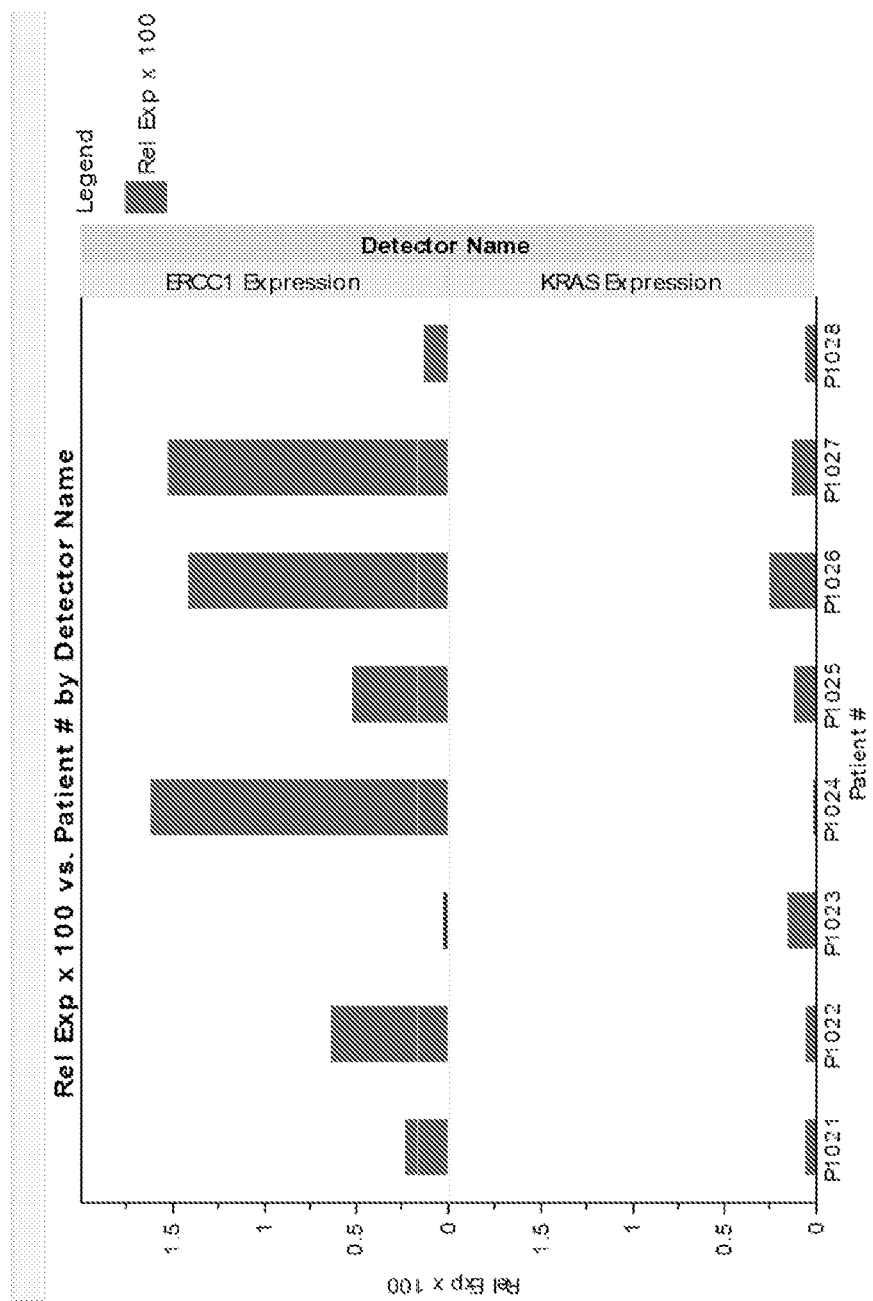
FIG. 1 shows the relative expression of ERCC1 and KRAS vs. beta actin from cell-free RNA extracted from colon cancer patient's plasma.

Blood from a colon cancer patient was drawn into tubes containing an RNA stabilizing agent (RNA BCT tubes from Streck) and stored overnight at room temperature. Plasma was separated by centrifugation and RNA was extracted using Qiagen Circulating Nucleic Acids nucleic acids kit. Relative gene expression was determined using a real-time Taqman platform (ABI 7900) with primers specific for ERCC1, KRAS WT and beta Actin. Calculations were made using a delta CT method between the level of the PCR products for the standard house-keeping gene, beta actin and the PCR products from ERCC1 and KRAS WT specific primers respectively. The results are shown in FIG. 1 which shows the relative expression of ERCC1 and KRAS vs. beta actin from cell free RNA extracted from colon cancer patient's plasma. FIG. 18 shows ERCC1 expression in patients with KRAS (red), NRAS (green), BRAF (yellow), or no (blue) mutations.

Example 3

Figure 2:
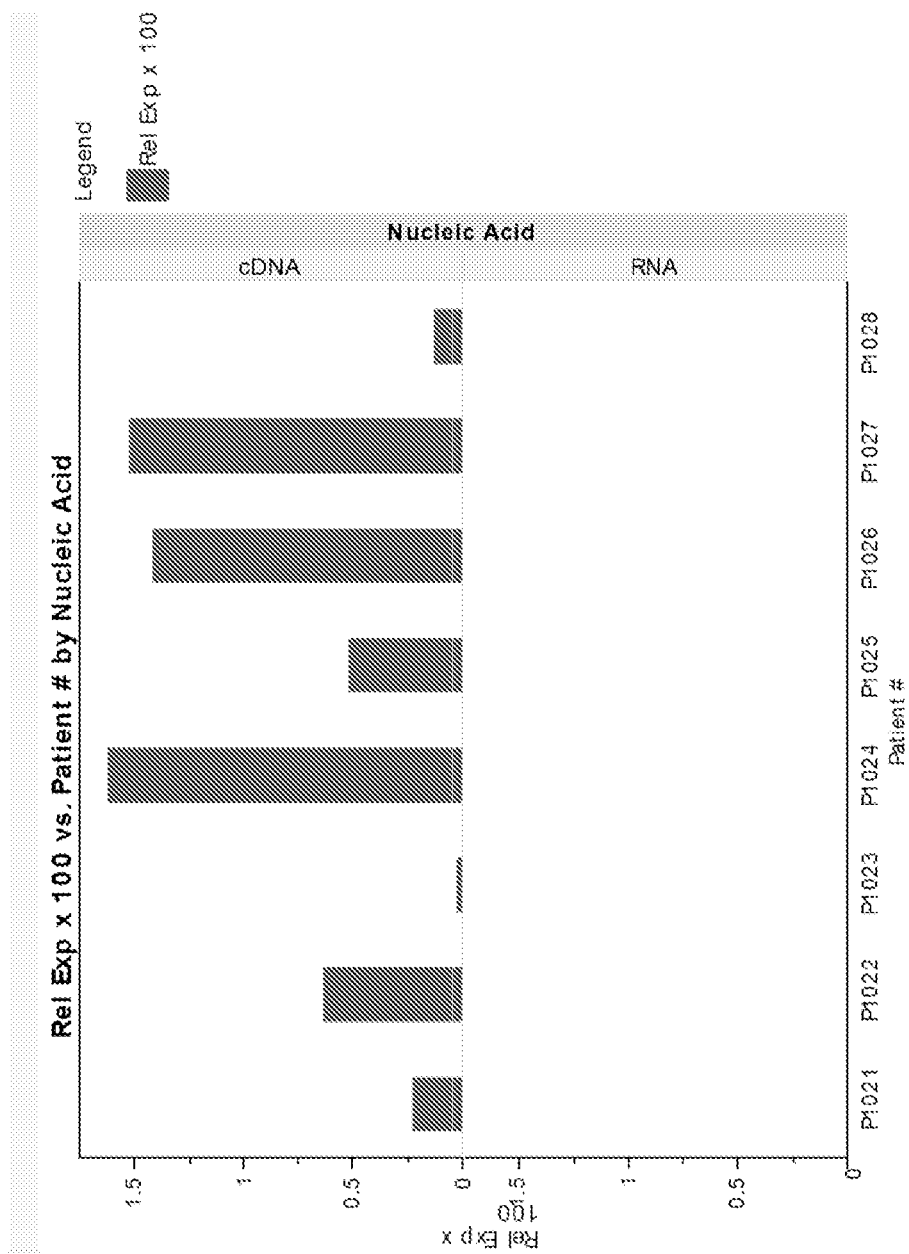
FIG. 2 shows the ERCC1 expression from colon cancer patient plasma.

The experiment described in this example assessed the possibility that the ERCC1 signal could be derived from residual DNA left over in the plasma after DNAse digestion. The top portion of the FIG. 2 shows the PCR expression panel using RNA that has been reverse-transcribed into cDNA. The bottom panel shows the negative results of amplifying the samples using non-reverse-transcribed RNA. Any amplification of residual DNA that would have contributed to the expression assay on the top panel would have produced a signal using non-reverse-transcribed RNA. The PCR signal is RNA specific and further shows that non-reverse-transcribed RNA (no-RT) generates no background PCR signal.

Example 4

Figure 3:
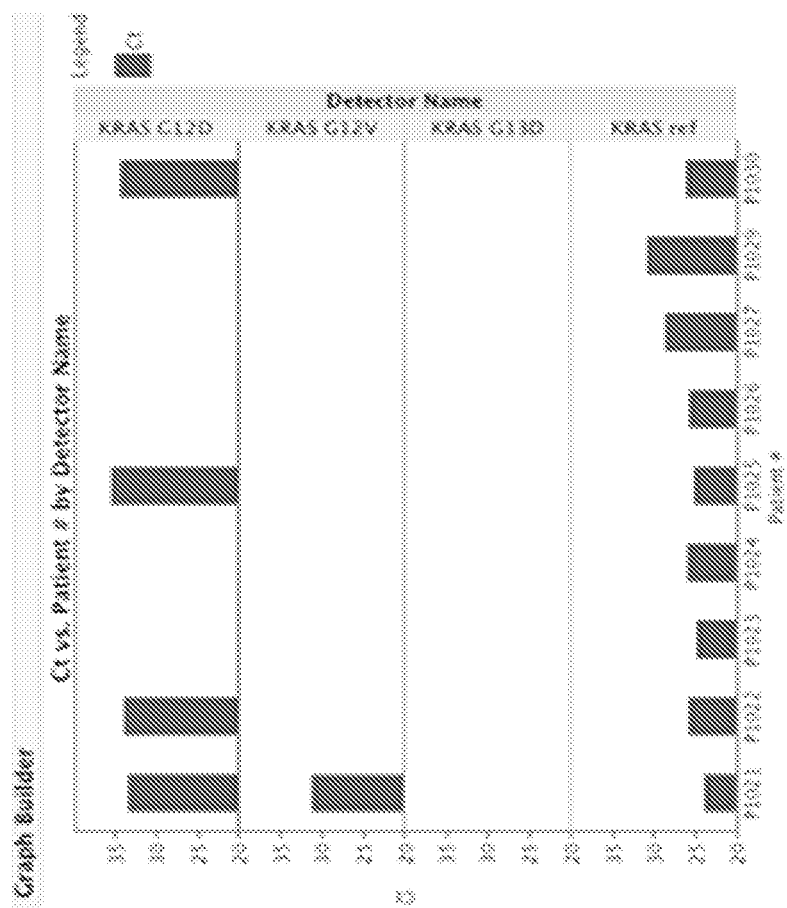
FIG. 3 shows DNA analysis for various allele fractions of G12D and G12V KRAS mutations in expected frequency and copy number assay for KRAS.

The experiment described in this example assessed the KRAS mutational status in DNA of the samples used to measure gene expression. As shown in FIG. 3, this data was generated to show that the samples in the study generally reflected the genetic mutation frequencies of KRAS in colon cancer. The expected frequency KRAS mutation variants were found in this set of samples as well as the appearance of KRAS reference wild-type gene levels. The most frequent KRAS mutation variant in colon cancer was KRAS G12D, followed by G12V and the less frequent G13D. Statistically, G12D and G12V mutants should have been identified in this small number of patients, whereas a larger number of patients would be needed to identify a G13D mutation. KRAS reference DNA was PCR amplified using an area of the gene devoid of mutations. All patient samples should contain KRAS reference DNA sequences.

Example 5

Figure 4:
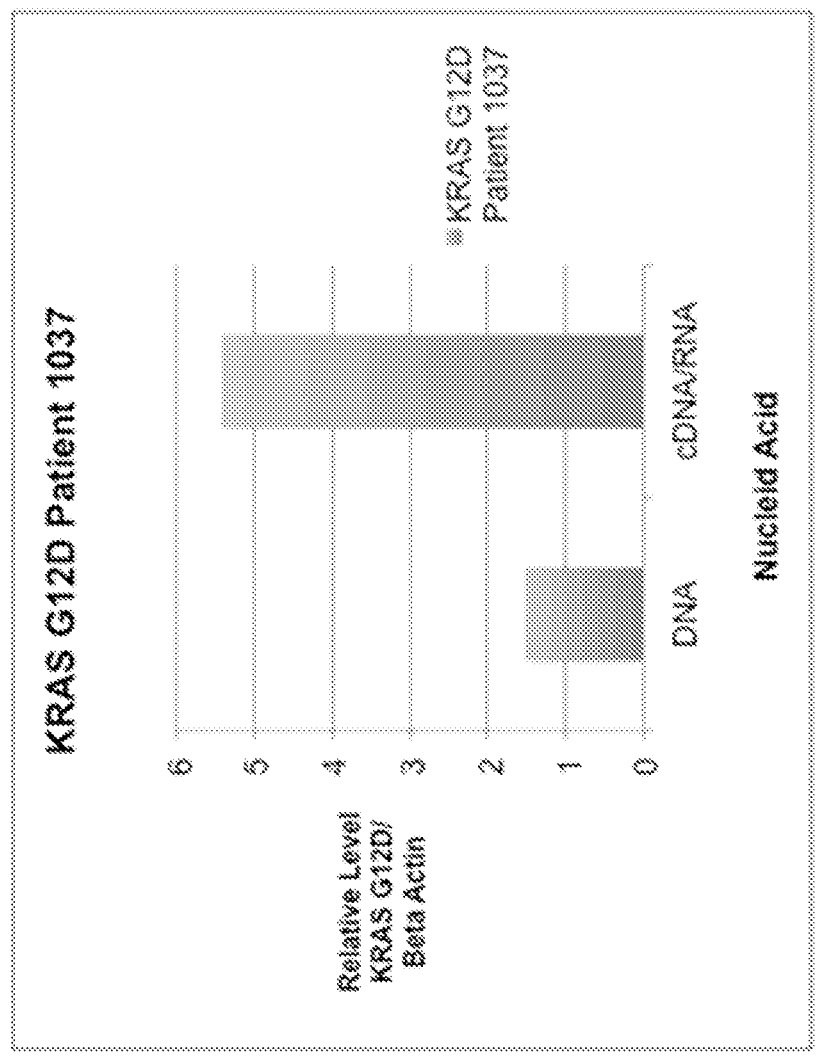
FIG. 4 shows the analysis of KRAS G12D mutation in a patient. The specific KRAS mutation determined from cell-free DNA is reflected in the RNA from the same patient.

In this example and as depicted in FIG. 4, a specific KRAS mutation determined from cell-free DNA was reflected in the RNA of the same patient. Cell-free DNA was exuded from the tumor into the blood stream. This example confirmed the hypothesis that if cell-free RNA was reflective of cell-free DNA from the tumor, then the mutation status for a gene should be concordant in these two nucleic acids. This was the case for the analysis of colon cancer patient 1037.

Further analysis for the presence of KRAS G12D mutation in patient 1037 can be was performed using digital PCR technology as a second platform.

Example 6

Figure 5:
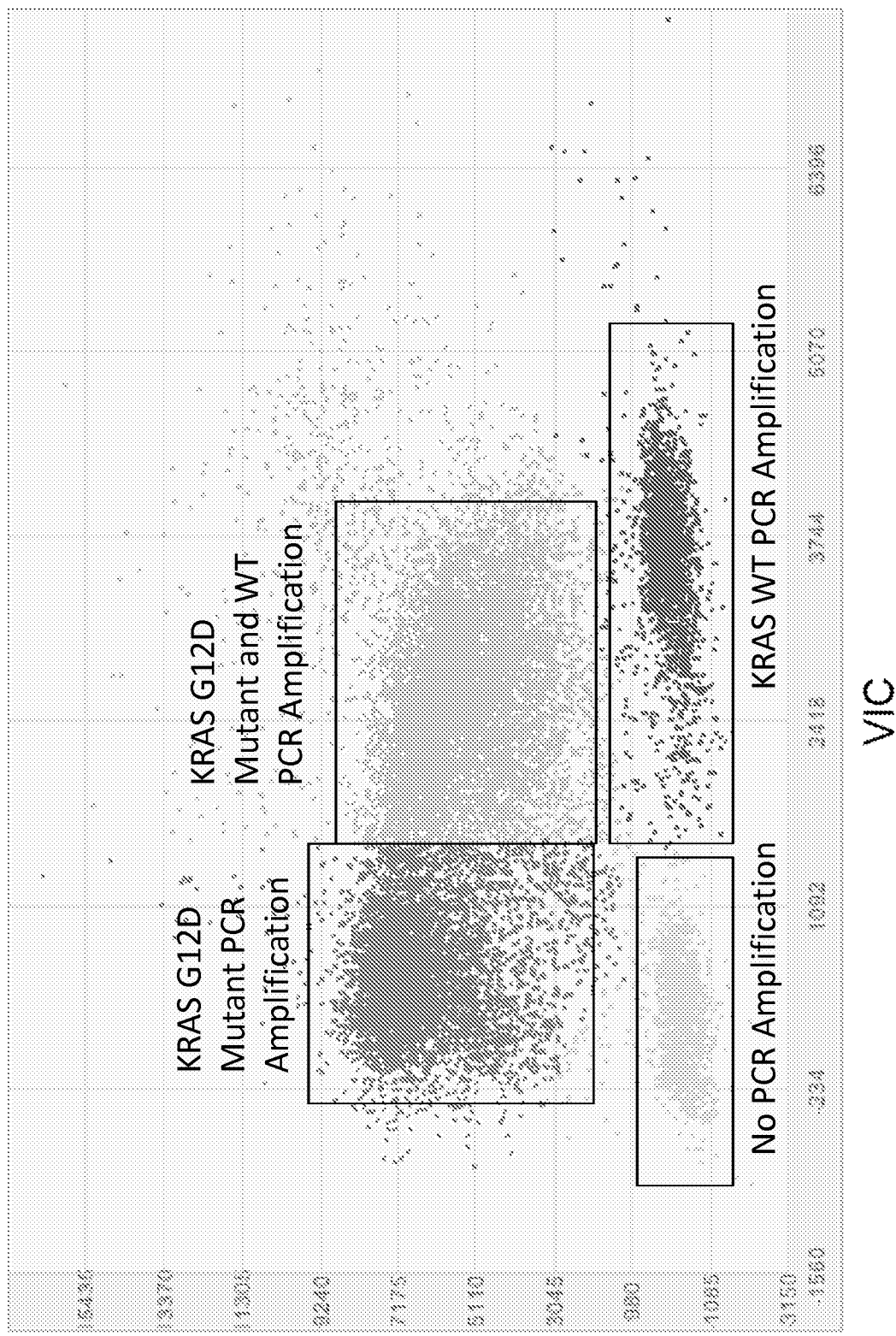
FIG. 5 shows the analysis of KRAS G12D mutation in a patient using digital PCR. The G12D KRAS mutation was validated again using a different platform. Several populations are delineated in the figure, in clockwise order from upper left—(1) KRAS G12D mutant PCR amplification, (2) KRAS G12D mutant and wild type PCR amplification, (3) KRAS wild type PCR amplification, and (4) no PCR amplification.

In this example and as depicted in FIG. 5, we were able to assess the percentage of KRAS mutant allele with respect to the wild type allele. For the purpose of this study, we used the second platform and second assay to validate the existence of the G12D KRAS mutation in this patient sample.

Figure 12:
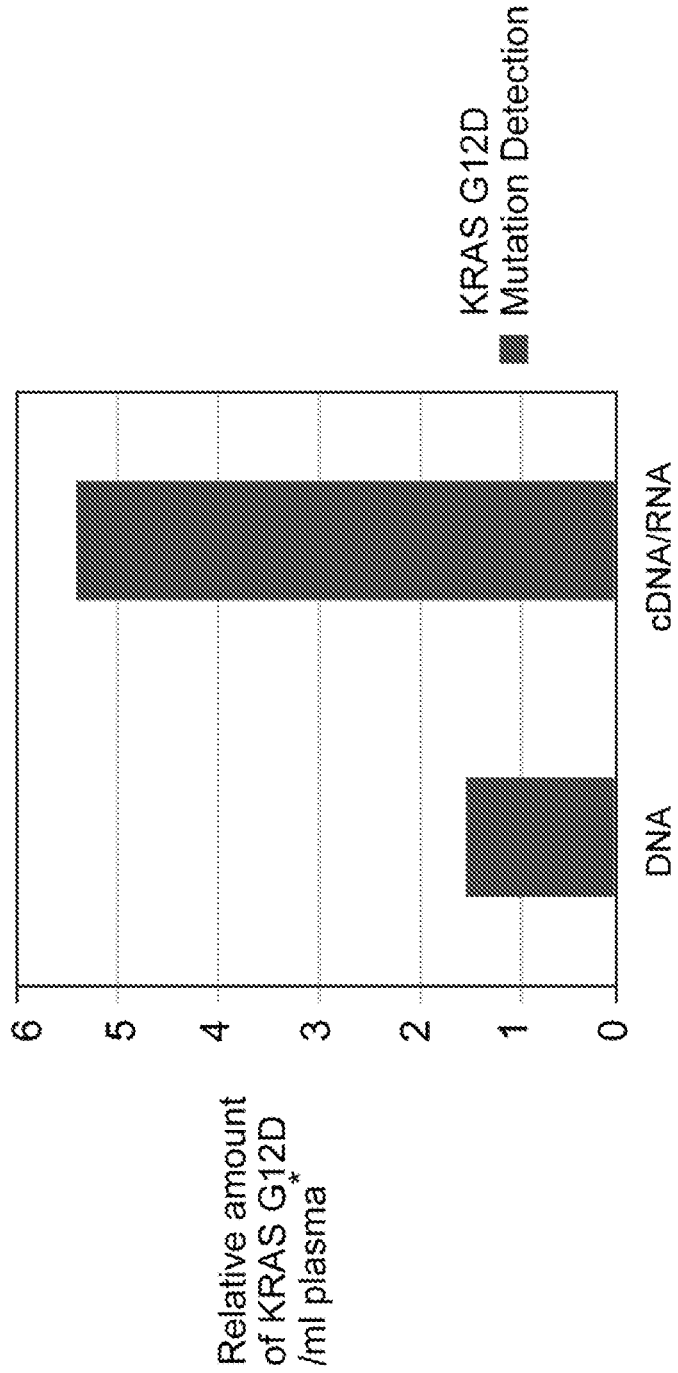
FIG. 12 shows results of relative KRAS G12D expression in a particular patient. Expression was measured by PCR analysis of KRAS G12D, using β-actin as a reference.

FIG. 12 shows the relative amount of KRAS G12D per mL of plasma in DNA and cDNA/RNA.

Allele-specific PCR primer probes with or without wild-type blocker primers were used to assess the mutational status of KRAS from colorectal cancer patient's plasma samples. The same results were obtained. In measuring mutations in cDNA reverse transcribed from RNA, allele-specific PCR primer probes were used. Additionally, wild-type blocker primers to further enhance the sensitivity of the signal from PCR amplification of RNA/cDNA are designed and used.

Figure 6:
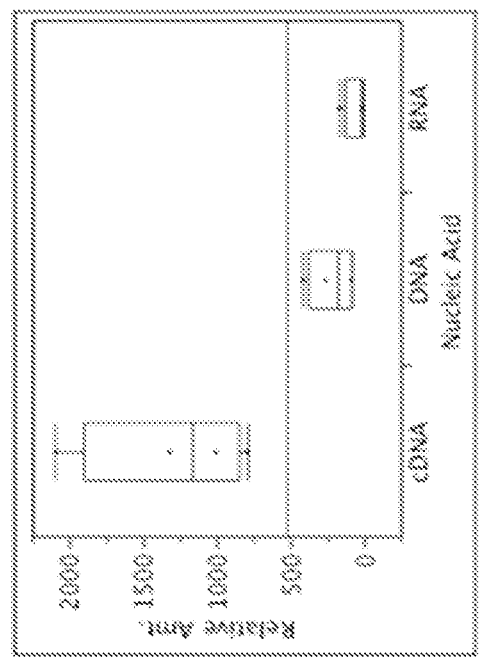
FIG. 6 shows the relationship in signal between RNA and DNA. The median PCR signal from reverse transcribed mRNA (cDNA) extracted from colon cancer patient's plasma was found to be approximately seven fold higher than the corresponding DNA.

Increased sensitivity and specificity can be obtained from the increased signal of RNA vs. DNA. Since there are multiple RNA fragments transcribed from DNA, we would expect the signal to be higher from PCR analysis of cDNA reverse transcribed from RNA vs genomic DNA. In FIG. 6, we show the relationship in signal between RNA and DNA. The median PCR signal from reverse transcribed mRNA (cDNA) extracted from colon cancer patient's plasma was approximately seven fold higher than the corresponding DNA. The non-reverse transcribed mRNA background was negligible.

Example 7

Figure 7:
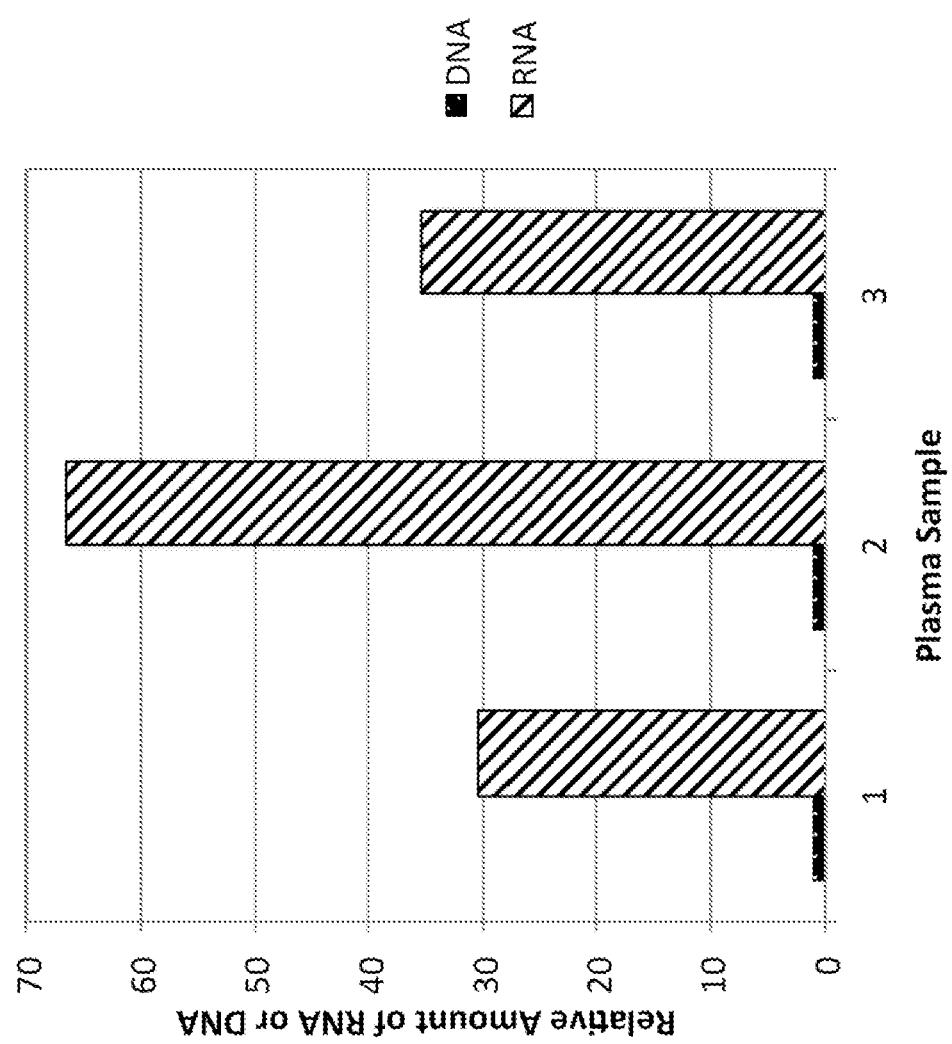
FIG. 7 shows results using column cDNA clean-up methods. The signal of RNA over DNA is further enhanced. The yield of RNA is approximately 60 fold higher than DNA.

Column cDNA clean-up methods were used to further enhance the signal of RNA over DNA. Without being bound by theory, the clean-up methods enhanced the signal of RNA by decreasing the inhibitory substances in the reverse transcription reactions and concentrated the cDNA. As shown in FIG. 7, the yield of RNA was up to 60 fold higher than DNA. Yield measured by relative beta-actin CTs per proportional volume of cDNA (RNA) vs DNA was extracted from the same patient plasma. Cycling parameters and reverse transcriptase clean-up reactions were adjusted to increase RNA signal.

Example 8

Cell-free DNA (cfDNA) released into the bloodstream by tumors allows non-invasive identification of initial tumor-specific mutations. However, not all molecular changes in tumors involve DNA mutations; in many cases it is also the quantity of a particular gene (i.e., gene expression) that is important. Cell-free RNA (cfRNA) released into the blood was measured in order to monitor PD-L1 gene expression in NSCLC patients. The PD-1/PD-L1 pathway is a promising therapeutic target and anti-PD-L1 agents have shown encouraging activity in a variety of tumor types.

Blood samples were collected from NSCLC patients at various times during therapy. Additionally, non-cancer bearing blood samples were obtained from healthy volunteers ("control group"). Plasma was fractionated from blood samples and nucleic acids were extracted. RNA was reverse-transcribed into cDNA using random primers, and then analyzed by quantitative RT-PCR using appropriate gene-specific primers. The cDNA of PD-L1 was quantitated in both cancer patients and the control group. ERCC1 expression was also quantitated as an example of a non-tumor-specific gene. β-actin expression was used as the denominator gene representing total RNA.

Figure 8:
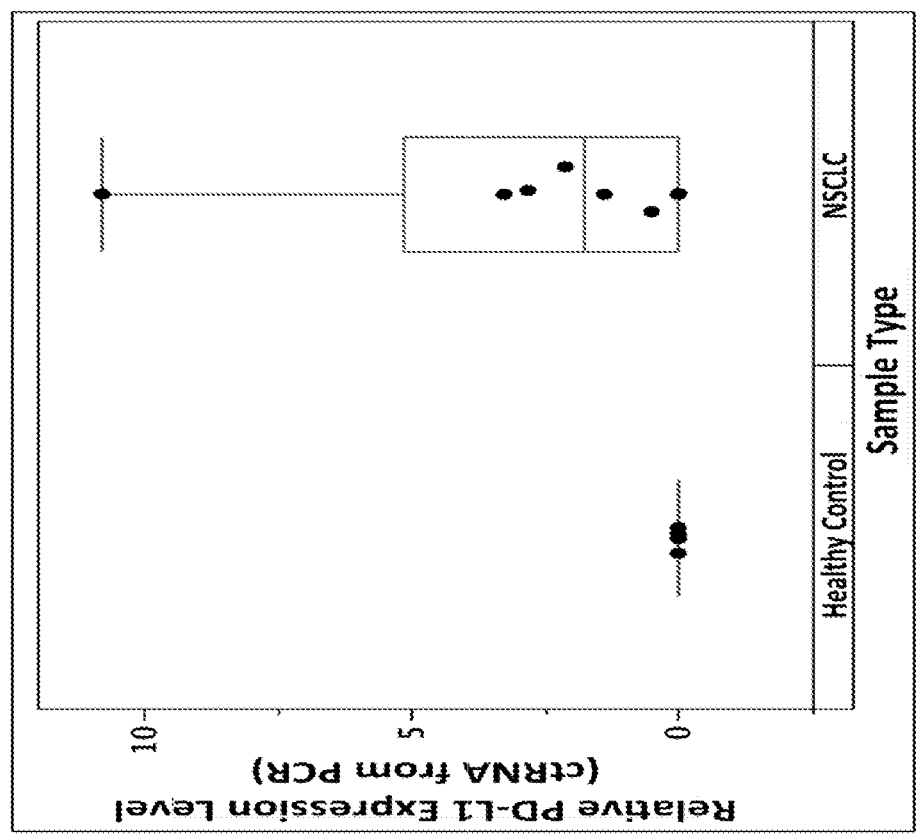
FIG. 8 shows results of relative PD-L1 expression across non-small cell lung cancer (NSCLC) patients and a healthy control group.
Figure 9:
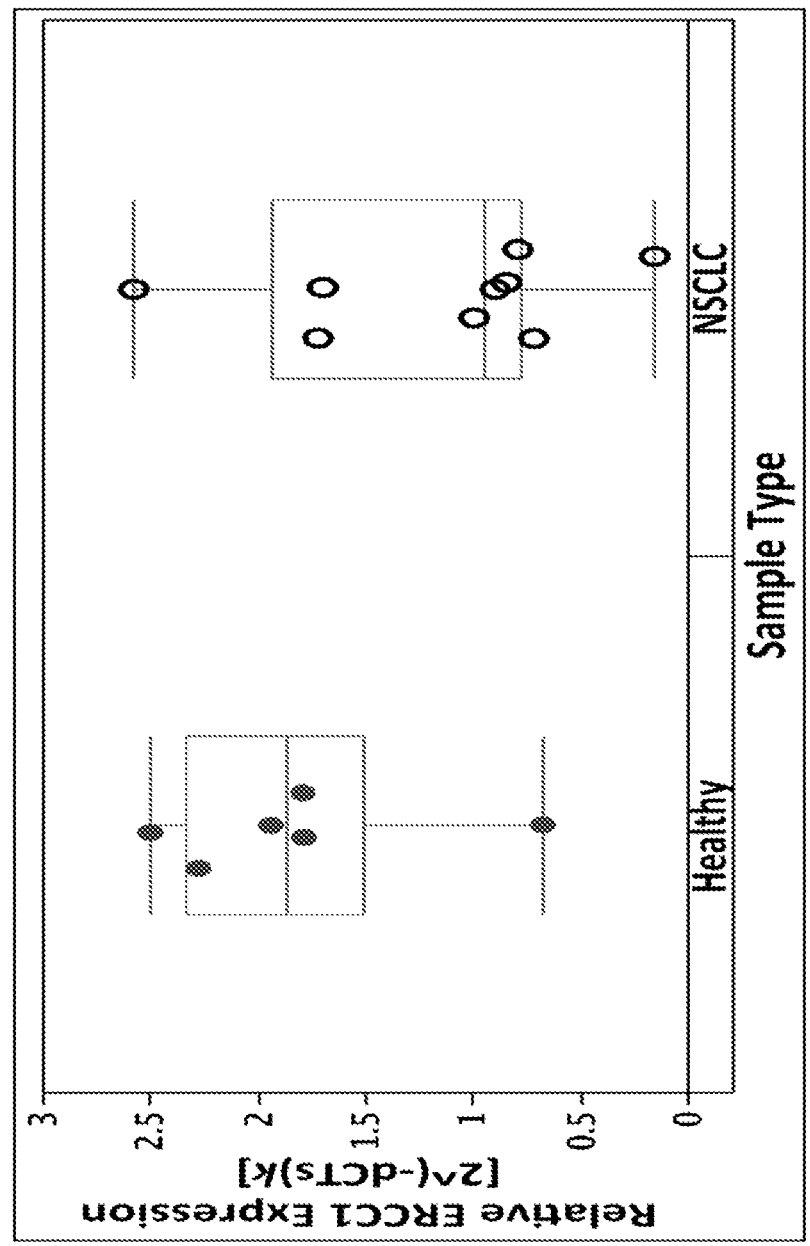
FIG. 9 shows results of relative ERCC1 expression across NSCLC patients and healthy control group.
Figure 10:
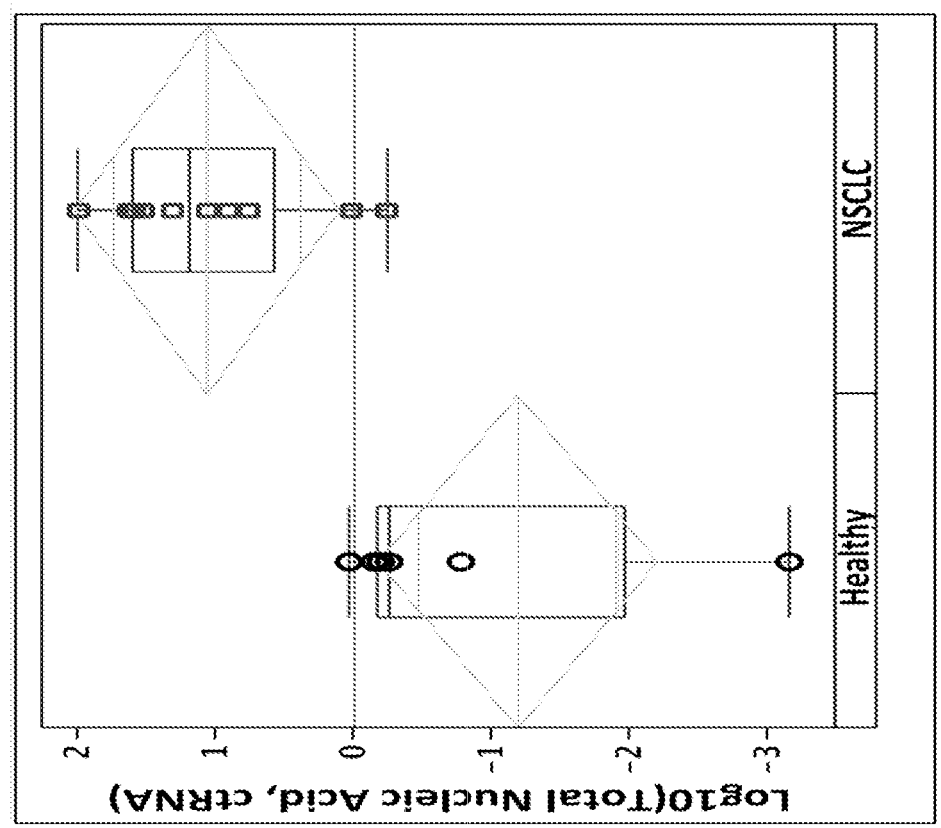
FIG. 10 shows results of total nucleic acid (ctRNA from β-actin CTs normalized by median) from NSCLC patients and a healthy control group.
Figure 11:
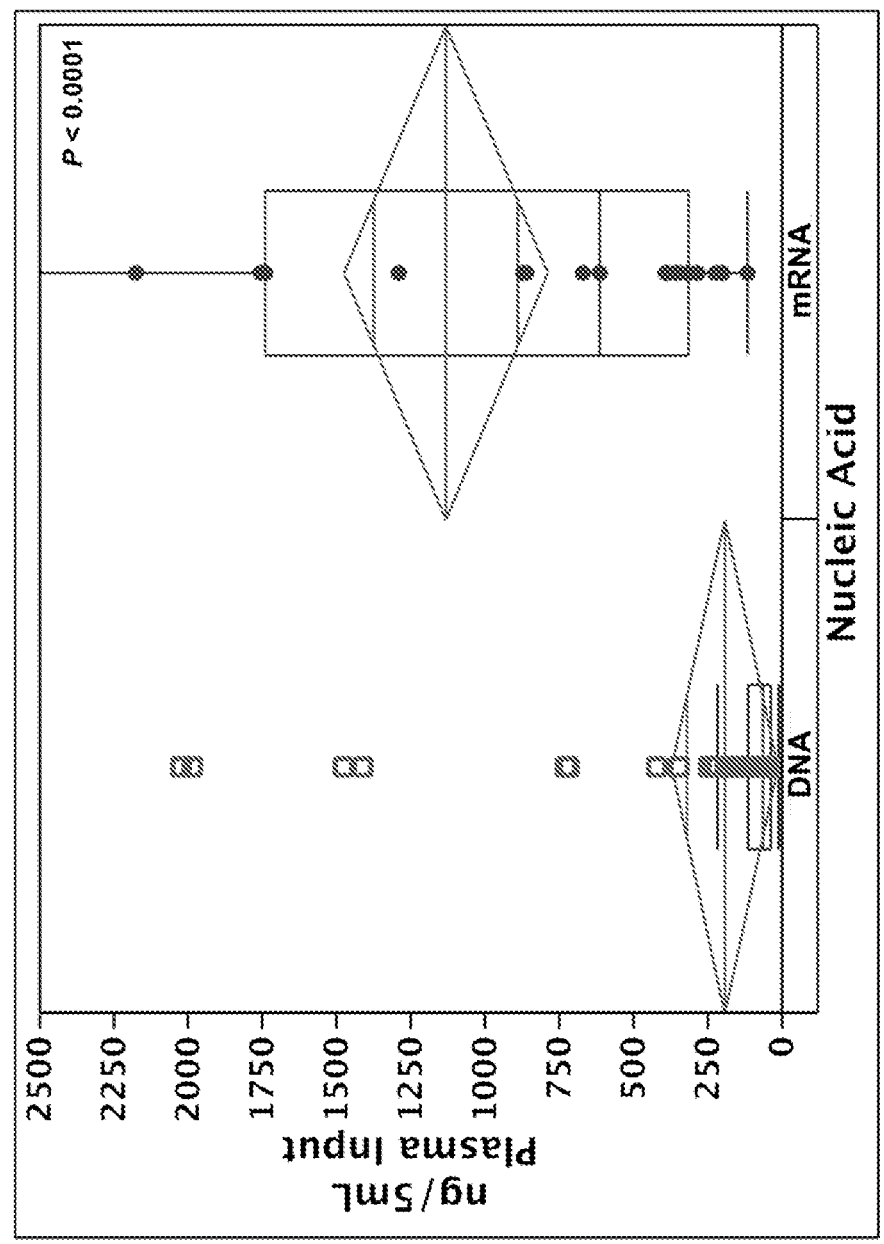
FIG. 11 shows the relationship in signal between DNA and mRNA. Median DNA signal is 59.63 ng/5 mL (range 5.88-2016.0 ng/5 mL). Median mRNA signal is 608.49 ng/5 mL (range 111.1-6312.02 ng/mL).

PD-L1 expression was detected in the ctRNA of 70% (7/10 plasma samples) of NSCLC patients, but was not detected in any samples from the control group (0/9), (p=0.0031, Fisher's Exact Test) (FIG. 8). ERCC1 expression was detected in 100% (10/10) of NSCLC patients and 67% (6/9) of the control group, with no significant difference observed in the relative expression of those detected (p=0.2328, Wilcoxon Rank Sums) (FIG. 9). Median relative β-actin expressions in cancer patients and the control group were 15.52 (0.54-94.91) and 0.53 (0-1.03), respectively (p=0.0008, Wilcoxon Rank Sums) (FIG. 10).

These data demonstrate the potential value of using cfRNA from blood to measure gene expressions for detection of cancer and its recurrence, and in selecting and monitoring therapies. The presence of PD-L1 cfRNA in blood may be a specific indicator of cancer, although its sensitivity of tumor detection is less than 100% because it is not expressed in all cancer patients. ERCC1 expression exemplifies a gene with no significant difference in expression level across cancer patients and healthy individuals. The surprisingly large (about 30-fold) difference in median total cfRNA between cancer patients and healthy individuals suggests that total cfRNA may be useful as a sensitive preliminary indicator of the presence of cancer and for recurrence monitoring. FIG. 14A shows the relative frequency of PD-L1 gene expression in colorectal cancer (CRC), non-small cell lung cancer patents (NSCLC) and healthy individuals, 17.4% of CRC patients, 50% of NSCLC patients, and 0% of healthy individuals have relative increases in PD-L1 expression. FIG. 14B shows that relative PD-L1 gene expression levels are similar between PD-L1 positive CRC and NSCLC patients.

Example 9

In non-small cell lung cancer (NSCLC),) several genetic changes that have clinical consequences for targeted treatment approaches have been identified. As for EGFR mutations, Mutations there are already options for more than one line of treatment. For those patients with secondary changes like the T790M-mediated resistance to EGFR inhibitors irreversible tyrosine kinase inhibitors (TKI) seem to be a promising alternative. These options may however be limited to missing proof of such changes as with progressing tumor burden patients may be susceptible to higher mortality with necessary invasive procedures. The so called "Liquid Biopsy"—using peripheral blood to obtain timely information on genetic information in solid malignancies—seems to be the urgently needed solution to this problem. Methods are needed that hold the promise of fast-turn around and broad availability.

Correlation of mutation detection results from serum correlated significantly with measurement of the available tumor specimen. Furthermore expected frequencies were in line with published occurrence of genetic changes. There was however a potential bias as T790M mutations were higher than expected which may be due to cancer center specific patient selection. These results were in line with the fresh blood samples tested. Turn-Around of fresh samples was three (3) days.

Mutation detection is feasible from peripheral blood with fast turn-around and high sensitivity and specificity. In addition samples can be used either fresh or as stored serum probes. This will allow faster treatment decisions and higher patient satisfaction due to shorter intervals until start of therapy. The method described herein for detecting mutations from liquid (e.g., serum or blood) is a clear and medically needed alternative to analyzing tissue samples. Especially in cases of secondary changes to tumors during systemic therapy this method will be crucial.

Example 10

In this example, methods of the present invention are utilized in dynamic testing across disease progression and treatment. FIG. 13B shows an expected decrease in PD-L1 expression in cfRNA over the course of treatment in a responding patient.

Figure 15:
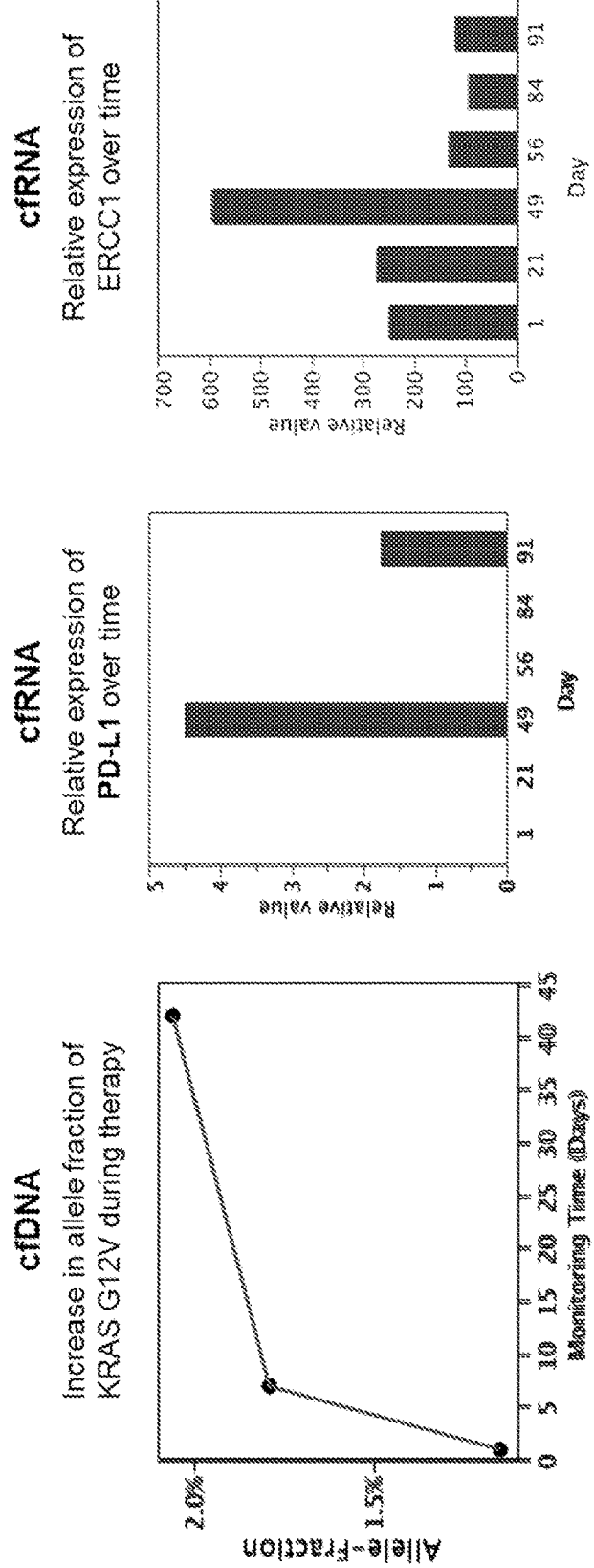

FIG. 15A shows an increase in allele fraction monitoring cfDNA for KRAS G12V throughout treatment of colorectal cancer with Regorafenib/Cetuximab. FIG. 15B shows that over time in the course of treatment there is a decrease in relative expression of PD-L1 in cfRNA during treatment of colorectal cancer with Regorafenib/Cetuximab. FIG. 15C shows the relative expression of ERCC1 over time during treatment of colorectal cancer with Regorafenib/Cetuximab.

FIG. 16 shows relative gene expression from cfRNA in colorectal cancer patients during treatment with crizotinib and FOLFOX for PD-L1, ERCC1, and KRAS G12D.

FIG. 17 shows relative gene expression from cfRNA in colorectal cancer patients during treatment with FOLFIRI/Bevacizumab and Regorafenib/Cetuximab for ERCC1, and KRAS G12D.

The methods of the present invention provide non, or less invasive ways to monitor disease progression or therapeutic response at time points prior to, throughout, and after treatment.

Furthermore, the methods can be used to assess relative gene expression in search of additional targets for therapy. For example, FIG. 19 shows relative expression monitored in cell-free RNA of PD-L1 and HER2 in a patient with gastric cancer. The data indicate an increase in PD-L1 and HER2 expression following initial monitoring presenting two additional targets for therapy.

What is claimed is:

1. A method for detecting PD-L1 mRNA in a blood sample from an individual, the method comprising:
   a. isolating cfRNA from the blood sample on a solid support, wherein the blood sample has been interacted with RNA stabilizer;
   b. digesting DNA from the biological sample while the cfRNA is on the solid support;
   c. eluting cfRNA at least once from the solid support;
   d. reverse transcribing the cfRNA to cDNA;
   e. reacting the cDNA with at least one primer that is specific for
      i. a PD-L1 gene mutation, or
      ii. a PD-L1 fusion transcript, or
      iii. PD-L1 gene expression.

2. The method of claim 1 wherein the eluate of step (c) is passed over the same column for a dual elution prior to the reverse transcribing the cfRNA to cDNA.

3. The method of claim 1 wherein the individual has or is suspected of having cancer.

4. The method of claim 3 wherein the plasma is processed within 7 days of interacting with the RNA stabilizer.

5. The method of claim 1 wherein random hexamers are used in step (d) to reverse transcribe the RNA to cDNA.

6. The method of claim 1, further comprising sequencing the cDNA.

7. The method of claim 6, wherein the sequencing comprises polymerase chain reaction (PCR)-based sequencing.

8. The method of claim 7, wherein the PCR-based sequencing is next generation sequencing.

\* \* \* \* \*